(12) United States Patent
Bornzin et al.

(10) Patent No.: US 9,241,638 B2
(45) Date of Patent: Jan. 26, 2016

(54) SYSTEM AND METHOD FOR IMPLANTING A PHYSIOLOGIC SENSOR ASSEMBLY

(75) Inventors: Gene A. Bornzin, Simi Valley, CA (US); John W. Poore, South Pasadena, CA (US); Zoltan Somogyi, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 856 days.

(21) Appl. No.: 13/464,590

(22) Filed: May 4, 2012

(65) Prior Publication Data

US 2013/0296661 A1 Nov. 7, 2013

(51) Int. Cl.
| | |
|---|---|
| *A61B 5/00* | (2006.01) |
| *A61B 5/0205* | (2006.01) |
| *A61B 5/0215* | (2006.01) |
| *A61B 5/042* | (2006.01) |
| *A61B 5/11* | (2006.01) |
| *A61B 5/145* | (2006.01) |

(52) U.S. Cl.
CPC ............. *A61B 5/0205* (2013.01); *A61B 5/0215* (2013.01); *A61B 5/042* (2013.01); *A61B 5/1116* (2013.01); *A61B 5/14532* (2013.01)

(58) Field of Classification Search
CPC combination set(s) only.
See application file for complete search history.

(56) References Cited

U.S. PATENT DOCUMENTS

| | | | |
|---|---|---|---|
| 4,702,735 A | 10/1987 | Luther | |
| 4,846,191 A | 7/1989 | Brockway et al. | |
| 2005/0115561 A1* | 6/2005 | Stahmann et al. | 128/200.24 |
| 2006/0079793 A1* | 4/2006 | Mann et al. | 600/486 |
| 2009/0076401 A1 | 3/2009 | Mazar et al. | |
| 2012/0059238 A1* | 3/2012 | Wolf | 600/377 |

FOREIGN PATENT DOCUMENTS

WO 2009036256 A1 3/2009

* cited by examiner

*Primary Examiner* — Michael Kahelin
*Assistant Examiner* — Mitchell E Alter

(57) ABSTRACT

An implantable physiologic sensor assembly is configured to be implanted within a patient. The assembly includes a module that houses an internal operative chamber, and a flexible pressure-detecting member connected to the module. The module and the pressure-detecting member are separated before implantation into the patient. At least a first end of the pressure-detecting member is configured to be inserted into an artery of the patient and a second end of the pressure-detecting member is connected to the module. The module is configured to be subcutaneously positioned within the patient.

16 Claims, 16 Drawing Sheets

US 9,241,638 B2

SYSTEM AND METHOD FOR IMPLANTING A PHYSIOLOGIC SENSOR ASSEMBLY

BACKGROUND OF THE INVENTION

Embodiments generally relate to a physiologic sensor assembly, and more particularly to a system and method for implanting a physiologic sensor assembly within a patient.

During routine medical visits, a physician or other medical personnel typically measure a patient's blood pressure. Patients that may be prone to cardiovascular issues, such as indicated by a family history of cardiovascular disease, are encouraged to monitor blood pressure regularly. Moreover, many patients that have cardiovascular issues are, in fact, monitored regularly for blood pressure. For example, individuals having hypertension (high blood pressure) typically are encouraged to be diligent in monitoring and controlling their blood pressure.

In general, blood pressure is the pressure exerted by circulating blood upon the walls of blood vessels. During each heartbeat, blood pressure varies between a maximum (systolic) and a minimum (diastolic) pressure. Typically, blood pressure decreases as the circulating blood moves away from the heart through arteries, due to pumping by the heart and resistance to flow in blood vessels. Blood pressure drops along the small arteries and arterioles, and continues to decrease as the blood moves through the capillaries and back to the heart through veins.

Often, a sphygmomanometer, or blood pressure meter, is used to measure blood pressure. A conventional sphygmomanometer generally includes an inflatable cuff that is used to restrict blood flow, and a mercury or mechanical meter used to measure the pressure. The cuff is usually positioned around an arm of an individual. Blood pressure is typically measured proximate a person's upper arm, such as on the inside of an elbow.

For individuals that require blood pressure monitoring around the clock, implantable blood pressure sensors have been used. Typically, implantable blood pressure sensors are implanted deep within an individual's body, such as within the heart or the pulmonary artery. In general, however, the process of implanting such blood pressure sensors is typically complex, and poses significant surgical risks.

SUMMARY

Embodiments provide a simple and efficient system and method of implanting a physiologic sensor assembly into a patient.

Certain embodiments provide an implantable physiologic sensor assembly configured to be implanted within a patient. The assembly may include a module that houses an internal operative chamber having a processing unit configured to sense at least one physiological attribute of the patient. The module is configured to be subcutaneously positioned within the patient.

The assembly also includes a flexible pressure-detecting member having a first end portion configured to be inserted into vasculature of the patient, and a second end portion that is connectable to the module. The pressure-detecting member is separated from the module while the first end portion is being inserted into the vasculature of the patient. The second end portion is connected to the module after the first end portion is inserted into the vasculature of the patient.

The internal operative chamber may include a flexible diaphragm that abuts the second end portion of the pressure-detecting member when the second end portion is connected to the module. The internal operative chamber may also include a transducer operatively connected to the flexible diaphragm. The transducer may be configured to detect pressure pulses from pumping blood within the vasculature of the patient that are transmitted into the pressure-detecting member.

The second end portion of the pressure-detecting member may include a rigid connector connected to a flexible sheath. The flexible sheath may include a flexible cannula.

The module may include a connector port configured to receive and securely retain the connector of the pressure-detecting member. One of the connector port or the connector may include a detent, and the other of the connector port or the connector may include a reciprocal groove configured to securely retain the detent so that the module is secured to the pressure-detecting member.

The connector port may include a needle tip, and a membrane configured to retain a pressure-transmitting fluid within the connector port prior to the connector port receiving and retaining the connector. The connector may include a membrane configured to retain a pressure-transmitting fluid within the pressure-detecting member prior to the connector port receiving and retaining the connector.

The assembly may also include at least one electrode extending from the module. The electrode(s) may be configured for use in connection with an electrocardiogram.

The internal operative chamber may also house a blood analyzer configured to monitor the glucose level of a blood sample. The module may also include a blood inlet port and a blood outlet port connected by a channel, wherein the blood analyzer is disposed within the channel.

The processing unit may be configured to detect pressure pulses transmitted from the pressure-detecting member. The internal operative chamber may also include a memory configured to store one or more of blood pressure data, electrocardiogram data, or blood glucose data. The internal operative chamber may also include at least one telemetry coil configured to communicate with an external device. The telemetry coil(s) may be configured to receive electromagnetic RF power signals to provide power to the assembly. The internal operative chamber may also include a posture-detecting device configured to detect a posture of the patient.

Certain embodiments provide a method of implanting a physiologic sensor assembly into a patient. The method may include introducing a hypodermic needle into vasculature of the patient at an injection site, moving a distal tip of a pressure-detecting member into a proximal end of the hypodermic needle, introducing a first end portion of the pressure-detecting member into the vasculature through the hypodermic needle, removing the hypodermic needle from a second end portion of the pressure-detecting member, making an incision proximate the injection site, forming a pocket through the incision, connecting a module to the second end portion of the pressure-detecting member to form the physiologic sensor assembly, and inserting the module into the pocket.

The method may also include positioning a remaining portion of the pressure-detecting member that is outside of the patient into one or both of the vasculature or the pocket, and closing the incision after the positioning.

The connecting may include inserting a rigid connector of the pressure-detecting member into a connector port of the module.

Certain embodiments provide a method of operating a physiologic sensor assembly that is implanted within a patient. The method may include monitoring blood pressure of the patient with the physiologic sensor assembly, performing an electrocardiogram (EKG) of the patient through electrodes extending from the physiologic sensor assembly, storing rolling short term frames of blood pressure and EKG data in a memory of the physiologic sensor assembly, and monitoring a posture of the patient with a posture-detecting device of the physiologic sensor assembly.

The method may also include recording blood pressure data and EKG data from a time prior to an abrupt change of posture detected by the posture-detecting device to a time after the abrupt change, storing data from the recording in a memory within the physiologic sensor assembly, and transferring the data from the memory to an external device through telemetry. The method may also include monitoring a blood glucose level of the patient with the physiologic sensor assembly.

Certain embodiments provide a method of implanting a physiologic sensor assembly into a patient. The method may include introducing a breakaway needle into vasculature of the patient at an injection site, moving a distal tip of a pressure-detecting member into a proximal end of the breakaway needle, introducing the pressure-detecting member into the vasculature through the breakaway needle, separating longitudinal halves of the breakaway needle from the pressure-detecting member, removing the longitudinal halves of the breakaway needle from the vasculature, making an incision proximate the injection site, forming a pocket through the incision, and inserting a module connected to the pressure-detecting member into the pocket.

The method may also include connecting the module to the pressure-detecting member. The method may also include integrally forming the module with the pressure-detecting member prior to the breakaway needle being inserted into the vasculature of the patient.

DETAILED DESCRIPTION

Figure 1A:
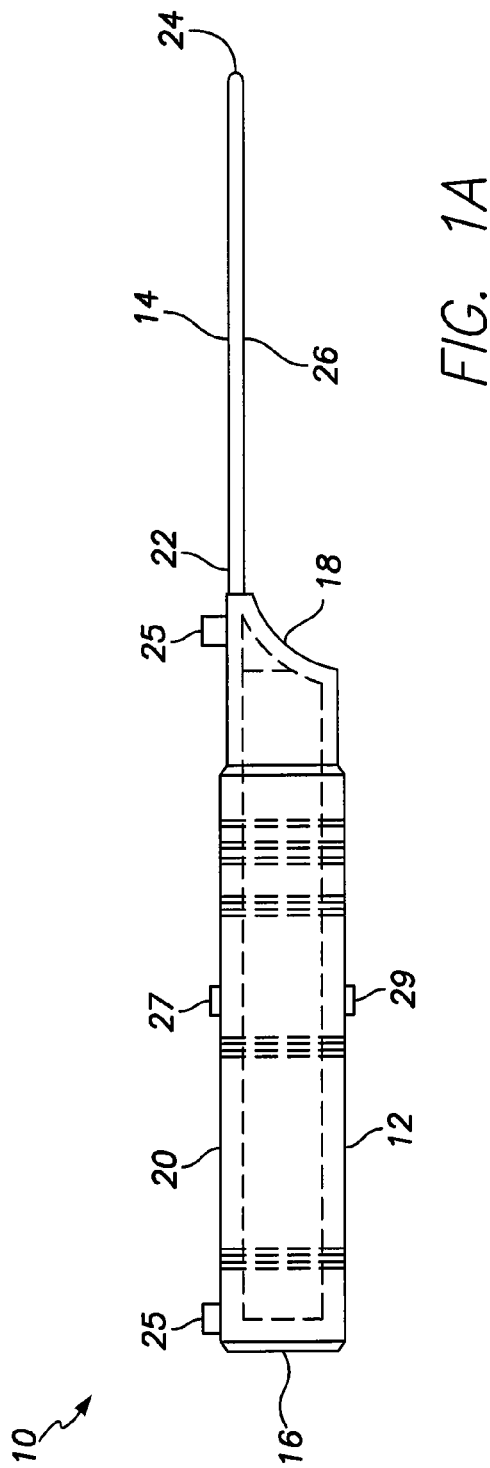
FIG. 1a illustrates a lateral view of a physiologic sensor assembly, according to an embodiment.

FIG. 1a illustrates a lateral view of a physiologic sensor assembly 10, according to an embodiment. The assembly 10 includes a housing or module 12 connected to a soft, flexible pressure-detecting member 14, such as a cannula, catheter, tube, or the like. The physiologic sensor assembly 10 is configured to sense, detect, or otherwise determined various physiological attributes of a patient, such as blood pressure, an electrocardiogram, blood glucose levels, and the like.

The module 12 may be shaped as a tube, block beam, or the like, with rounded, smooth surfaces, and has a proximal end 16 connected to a distal end 18 through a longitudinal, slender main body 20. A proximal end 22 of the pressure-detecting member 14 is received and retained at the distal end 16 of the module 12. The module 12 contains and protects an internal operative chamber, as discussed below. The module 12 is configured to be implanted within an individual, such as within a subcutaneous pocket underneath the skin, or secured to patient anatomy, such as a clavicle. The module 12 is shaped and sized to be comfortably secured within a subcutaneous pocket formed in a patient, on internal patient anatomy, such as a bone, or the like.

The pressure-detecting member 14 includes a long, flexible, deflectable tubular structure, such as a cannula, catheter, or the like. The pressure-detecting member 14 has an outer envelope that is shaped and dimensioned to be received in a hypodermic needle, syringe, or the like, for example. The proximal end 22 is securely retained within the distal end 16 of the module 12. The proximal end 22 of the pressure-detecting member connects to a distal tip 24 through a flexible, deflectable, longitudinal sheath 26 that is configured to be positioned within vasculature, such as an artery, vein, organ (such as the heart), or the like, of a patient. The sheath 26 retains a pressure-transmitting fluid, such as silicone gel, that is configured to transmit pressure pulses therethrough. Thus, when positioned within an artery, for example, pressure pulses of flowing blood within the artery are translated to the sheath 26. The pressure pulses are then transmitted through the length of the sheath 26.

The module 12 may also include one or more electrodes 25 extending outwardly therefrom. The electrodes 25 are configured to abut against patient anatomy, such as underneath skin proximate the chest, for example. The electrodes 25 may be used to detect an electrocardiogram (ECG or EKG) of a patient. The electrodes 25 may be separated from one another. The separation of the electrodes 25 is configured to provide a robust EKG signal. As shown in FIG. 1a, one electrode 25 may be positioned proximate the proximal end 22, while the other electrode 25 may be positioned proximate the distal end 16. However, the electrodes 25 may be positioned at various other positions on the module 12. In general, an EKG is a test that records the electrical activity of the heart. An EKG is used to measure the rate and regularity of heartbeats, as well as the size and position of the heart chambers, the presence of any damage to the heart, and the effects of drugs or devices, such as pacemakers, used to regulate the heart. The electrodes 25 are configured to abut against internal surfaces within a patient and are in electrical communication with a processing unit or control block (not shown in FIG. 1a) within the module 12.

An EKG detects and amplifies electrical changes within internal anatomy of the patient that are caused when heart muscle depolarizes during each heartbeat. At rest, each heart muscle cell has a negative charge (membrane potential) across its outer wall (or cell membrane). Increasing the negative charge towards zero (via the influx of the positive ions, Na+ and Ca++) is referred to as depolarization, which activates the mechanisms in the cell that cause it to contract. During each heartbeat, a healthy heart has an orderly progression of a wave of depolarization that is triggered by the cells in the sinoatrial node, spreads out through the atrium, passes through intrinsic conduction pathways, and then spreads over the ventricles. The wave progression is detected as tiny rises and falls in the voltage between the electrodes 25. The output from the electrodes 25 is then sent to the processing unit, which may store the data in memory, and ultimately transmit the data to an external device through telemetry.

The module 12 may also include a blood inlet port 27, which is connected to an internal blood analyzer within the module 12. The blood inlet port 27 may periodically or continuously receive blood samples of a patient. The blood samples may then be run through the internal blood analyzer to determine a blood glucose level. After the blood sample passes through the blood analyzer, the blood sample may then be passed out of the module through a blood outlet port 29. As such, the module 12 may continuously analyze the blood of a patient to determine whether any diabetic conditions exist.

Optionally, instead of a blood inlet port 27 and a blood outlet port 29, the module 12 may instead include a diffusion membrane in place of the port 27. The diffusion membrane may be formed of microporous polypropylene or 2-hydroxyethylene methacrylate, for example. The diffusion membrane may be configured to allow interstitial body fluid, which includes a glucose concentration representative of blood glucose, to diffuse therethrough into an internal blood analyzer within the module 12. The diffusion membrane is configured to allow glucose levels to be periodically or continually analyzed by the internal blood analyzer in order to determine an interstitial glucose level, which generally tracks blood glucose levels. Accordingly, the module 12 may continuously analyze the interstitial fluid of a patient to determine whether any diabetic conditions exist.

Alternatively, the blood inlet port 27 or membrane may be formed proximate the distal tip 24 of the pressure-detecting member 14. In this embodiment, the blood inlet port 27 or membrane is in fluid communication with an internal, insulated, and fluid-impermeable tube within the sheath 26 that connects to the internal blood analyzer.

Figure 1B:
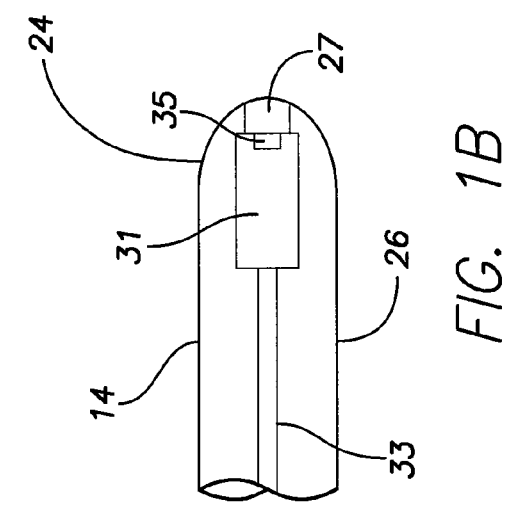
FIG. 1b illustrates an internal cross-sectional view of a distal tip 24 of a pressure-detecting member, according to an embodiment.

FIG. 1b illustrates an internal cross-sectional view of the distal tip 24 of the pressure-detecting member 14, according to an embodiment. As shown in FIG. 1b, the blood inlet port 27 or membrane may be positioned at the distal tip 24. However, the blood inlet port 27 or membrane may be positioned at various other locations along the sheath 26. The blood inlet port 27 or membrane may be in communication with a reservoir 31 within the pressure-detecting member 14. The reservoir 31 may, in turn, be connection to a fluid-impermeable tube 33 that connects to the internal blood analyzer.

The reservoir 31 may contain an anticoagulant solution, such as heparin or calcium nitrate solution. The reservoir 31 may include a septum 35, which may be formed of silicone rubber, for example. The reservoir 31 connects to the blood inlet port 27 or membrane through the septum 35.

As blood enters the blood inlet port 27 or membrane, the blood passes through the reservoir 31 containing the anticoagulant solution. The anticoagulant solution prevents the blood from coagulating within the physiologic sensor assembly 10. In order to replenish the anticoagulant solution within the reservoir 31, a small gauge needle connected to a syringe may pierce the septum so that additional solution within the syringe may be injected into the reservoir 31.

Figure 2A:
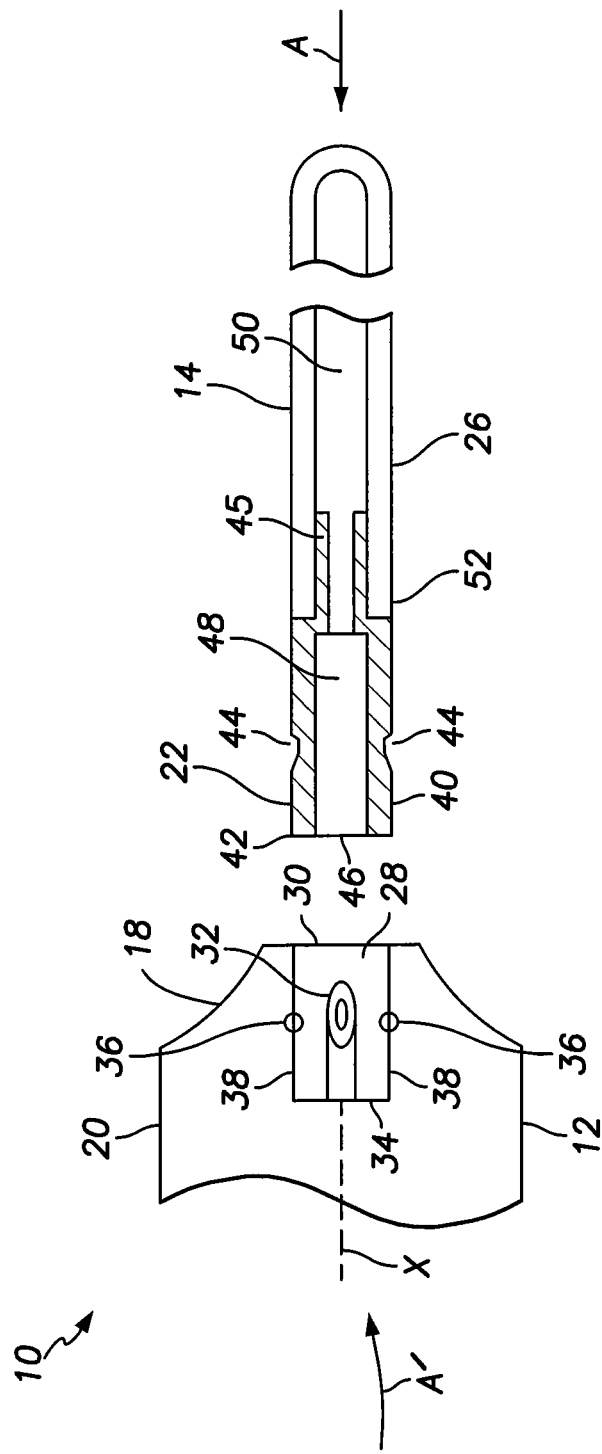
FIG. 2a illustrates a transverse cross-sectional view of a housing of a physiologic sensor assembly separated from a pressure-detecting member, according to an embodiment.

FIG. 2a illustrates a transverse cross-sectional view of the module 12 of the physiologic sensor assembly 10 separated from the pressure-detecting member 14, according to an embodiment. The pressure-detecting member 14 may be configured to be initially separated from the module 12 in order to allow the pressure-detecting member 14 to be injected into vasculature of a patient through a hypodermic needle, syringe, or the like. Once the pressure-detecting member 14 is injected into the patient anatomy, the pressure-detecting member 14 is coupled to the module 12, which may be separately secured within the patient, such as within a pocket formed in the chest of the patient. Alternatively, the module 12 and the pressure-detecting member 14 may be integrally formed as a single unit. For example, the pressure-detecting member 14 and the module 12 may be permanently affixed together, or formed as a single integral unit. The single unitary physiologic sensor assembly may be simpler to assemble than the two-piece assembly shown because the unitary construction does not include separable connection interfaces between the module 12 and the pressure-detecting member 14.

A connection port 28, such as a channel, recess, cavity, or the like may be formed within the distal end 18 of the module 12. The connection port 28 may be centered about a longitudinal axis X of the module 12. Optionally, the connection port 28 may be positioned at various other areas of the module 12. The connection port 28 is configured to receive and retain the proximal end 22 of the pressure-detecting member 14. A fluid-impermeable membrane 30 is positioned over the connection port 28 and serves to retain a pressure-transmitting fluid, such as liquid, gel, or the like, such as silicone gel, within the connection port 28.

A needle tip 32 extends from a base 34 of the recess toward the membrane 30. The needle tip 32 may be centered about the axis X of the module 12. Detents 36, such as spring members, ridges, clasps, barbs, semi-spherical nubs, or other such protuberances, extend from walls 38 on either side of the needle tip 32. For example, the detents 36 may include an annular spring member that rings around the internal circumference of the walls 38.

The pressure-detecting member 14 includes a rigid connector 40 at the proximal end 22. The rigid connector 40 may be formed of hard plastic, metal, or the like, and is configured to securely connect to the module 12 within the connection port 28. The connector 40 includes a port end 42 connected to a sheath-insertion tip 45. The port end 42 is configured to be received and retained within the connection port 28, while the sheath-insertion tip 45 is configured to securely fix within the flexible sheath 26. The connector 40 also includes a circumferential groove 44 that is configured to receive and retain the detents 36 within the connection port 28 in order to secure the pressure-detecting member 14 to the module 12.

A fluid-impermeable membrane 46 is positioned on the port end 42 of the connector 40 and is configured to retain a pressure-transmitting fluid, such as liquid, gel, or the like, such as silicone gel, within an internal, longitudinal channel 48 of the connector 40 and a longitudinal channel 50 of the sheath 26, which is in fluid communication with the channel 48. Optionally, the pressure-transmitting liquid may be water or oil, for example. In short, the pressure-transmitting liquid is configured to allow a pressure pulse, such as a pressure pulse transmitted into the sheath 26 through pumping blood, to transmit therethrough. Alternatively, instead of having a closed distal end, the sheath 26 may be open-ended but be filled with a silicone gel, which is configured to transmit pressure pulses. The thickness of the gel within the sheath 26 is chosen to prevent the gel from flowing out into the blood. Also, alternatively, a thick gel may be used to form a plug at the distal end of the sheath 26. Silicone oil having a relatively low viscosity may be contained within the sheath 26 (and prevented from flowing out into the blood by the relatively thick silicone gel at the distal end) is then used to transmit pressure pulses through the sheath 26.

As shown, the sheath-insertion tip 45 has a smaller diameter than the port end 42 of the connector 40. The sheath-insertion tip 45 fits within the longitudinal channel 50 of the sheath 26 at a proximal end 52 of the sheath 26. The sheath 26 is secured to the sheath-insertion tip 45, such as through permanent bonding, or the like, so that fluid does not leak through a connection interface therebetween. Alternatively, the sheath-insertion tip 45 may have a diameter that exceeds that of the sheath 26, and the sheath 26 may fit within the sheath-insertion tip 45.

As noted above, the pressure-transmitting fluid is contained within the pressure-detecting member 14 through the membrane 46 and the flexible, fluid impermeable sheath 26. The pressure-transmitting fluid provides a pressure transfer medium from the distal tip 24 of the sheath 26 to the membrane 46 located at the port end 42 of the connector 40. Similarly, the pressure-transmitting fluid within the connection port 28 provides a pressure transfer medium from the membrane 30 to a diaphragm (not shown in FIG. 2a) that abuts or forms the base 34 of the connection port 28. Therefore, when the pressure-detecting member 14 is coupled to the module 12 within the connection port 28, the pressure transmitting fluid within both the connection port 28 and the pressure-detecting member 14 provides a pressure transfer medium from the distal tip 24 of the sheath 26 to the diaphragm that abuts, or forms, the base 34 of the connection port 28.

In order to connect the pressure-detecting member 14 to the housing, the port end 42 of the pressure-detecting member 14 is aligned with the connection port 28 of the module 12. Then, the pressure-detecting member 14 is urged into the connection port 28 in the direction of arrow A, or the module 12 is urged into the port end 42 in the direction of arrow A'.

As the port end 42 of the pressure-detecting member 14 is mated into the connector port 28, the membrane 46 of the pressure-detecting member 14 abuts the membrane 30 sealing the connector port 28. With continued urging, the flexible membranes 46 and 30 are pushed toward the needle tip 32. When the flexible membranes 46 and 30 encounter the needle tip 32, the needle tip 32 pierces the membranes 30 and 46, thereby allowing the pressure-transmitting gel within the connector port 28 and the pressure-detecting member 14 to mix and freely flow therebetween. The pierced membranes 30 and 46 form an internal sealing member at the interface of the connector port 28 and the connector 40 that prevents the pressure-transmitting gel from escaping from the module 12 and the pressure-detecting member 14 proximate the interface.

As the needle tip 32 pierces the membranes 30 and 46, the detents 36 deflect into the groove 44 formed in the connector 40. In this manner, the detents lock the pressure-detecting member 14 to the module 12. Alternatively, the detents 36 may be located on the connector 40, while the groove 44 is formed within the connector port 28. Also, alternatively, instead of a detent-groove interface, the module 12 may secure to the pressure-detecting member 14 through various other interfaces, such as a threadable interface in which the module 12 and the pressure-detecting member 14 are rotated into threadable, locking engagement, a latching interface, an interference fit, or the like.

Additionally, alternatively, the connector port 28 may not include the membrane 30, and may not initially contain the pressure-tranmissive fluid before the pressure-detecting member 14 is secured to the module 12. Instead, the pressure transmitting fluid may be initially contained within the pressure-detecting member 14. As the pressure-detecting member 14 is mated into the connector port 28, the needle tip 32 pierces the membrane 46, and the pressure transmitting fluid flows freely between the connector port 28 and the channels 48 and 50.

Figure 2B:
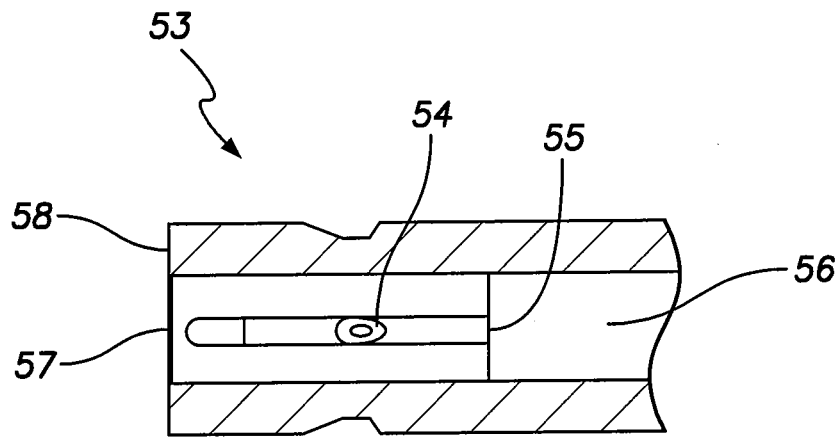
FIG. 2b illustrates a transverse cross-sectional view of a connector of a pressure-detecting member, according to an embodiment.

FIG. 2b illustrates a transverse cross-sectional view of a connector 53, according to an embodiment. In this embodiment, a needle tip 54 is supported by internal braces 55 within a channel 56. The braces 55 suspend the tip of the needle proximate a membrane 57.

Figure 2C:
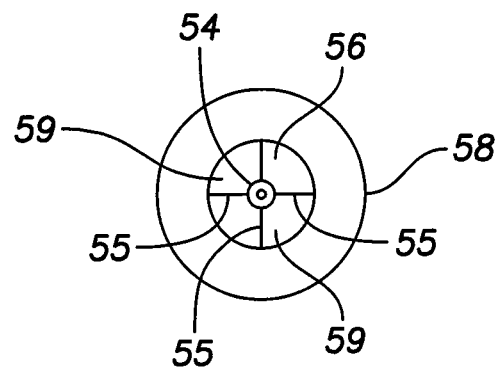
FIG. 2c illustrates an axial view of a port end of a connector of a pressure-detecting member, according to an embodiment.

FIG. 2c illustrates an axial view of a port end 58 of the connector 53, according to an embodiment. For clarity, the membrane 57 is not shown in FIG. 2c. As shown, the braces 55 rigidly suspend the needle tip 54 within the channel 56. The needle tip 54 may be coaxial with the connector 53. Fluid flow gaps 59 are positioned between neighboring braces 55. As such, the pressure transmitting fluid may flow around the needle tip 54. While the braces 55 are shown in a cruciform pattern such that a brace is positioned at 90 degree intervals within the channel 56, more or less braces 55 may be used. For example, the needle tip 54 may be supported by two braces 55 separated from one another by 180 degrees, thereby forming a straight line.

In operation, as the connector 53 is mated into the connector port 28 (without the needle tip), the membrane 30 over the connector port 28 abuts against the membrane 57, forcing both membranes 30 and 57 into the needle tip 54, which then pierces the membranes 30 and 57 and allows the pressure transmitting fluid to flow freely therebetween.

Figure 3:
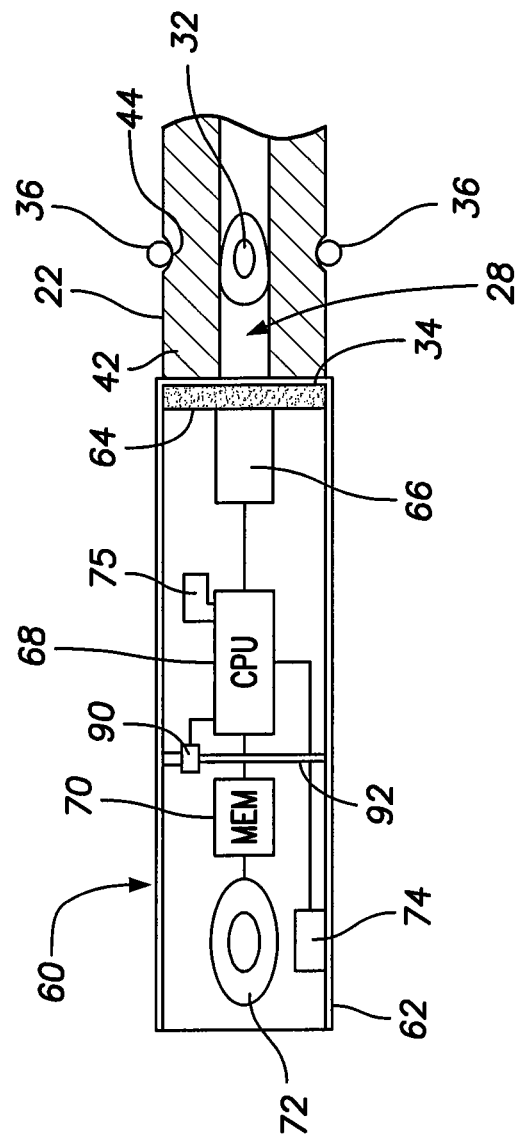
FIG. 3 illustrates a simplified diagram of an internal operative chamber within a module of a physiologic sensor assembly, according to an embodiment.

FIG. 3 illustrates a simplified diagram of an internal operative chamber 60 within the module 12 of the physiologic sensor assembly 10, according to an embodiment. The chamber 60 may be defined by a protective housing 62 that prevents liquid, gel, moisture, or the like from infiltrating into the chamber 60. The housing 62 may be formed of various hard plastics or metals, such as Titanium, for example.

A fluid-impermeable diaphragm 64 is located at one end of the chamber 60. The diaphragm 64 may form the base 34 of the connector port 28, or may optionally abut against a pressure-transmitting wall that forms the base 34. The diaphragm 64 prevents the pressure-transmitting fluid within the connector port 28 from infiltrating into the chamber 60. At the same time, the diaphragm 64 receives pressure pulses that are received and transmitted from the pressure-detecting member 14. The diaphragm 64 is flexible, resilient and transmits the received pressure pulses to a transducer 66, such as a piezoelectric strain gauge transducer that is bonded to or abuts against the diaphragm 64.

The transducer 66 is, in turn, electrically connected to a central processing unit or control block 68, which may include a microprocessor, integrated circuit, or the like. The transducer 66 transmits the received pressure pulses and electrically delivers the pulses to the processing unit 68, which then determines blood pressure of the patient based on the received pulses. The processing unit 68 is also in communication with a memory 70, having long-term and short term memory areas. The processing unit 68 may store pressure data within the memory 70. The processing unit 68 may also be in communication with the electrodes 25 (shown in FIG. 1). Therefore, the processing unit 68 may also determine an EKG of a patient, based on received signals, and then store the EKG data in the memory 70.

The components within the processing unit 68 and related functions may vary depending upon a particular implementation. By way of example, the processing unit 68 may include all of the control logic needed to implement the physiologic sensor assembly 10, such as but not limited to a blood pressure monitor, EKG system, blood glucose analyzer, and the like.

The chamber 60 also contains at least one telemetry coil 72 that is in communication with the processing unit 68 and the memory 70. As explained below, the telemetry coil(s) 72 are used to communicate with a remote system or external device in order to transmit blood pressure data, EKG data, and the like to the remote system or external device.

The chamber 60 may also include a posture-detecting device 74, such as an accelerometer, inclinometer, potentiometer, or the like, that is configured to detect changes in the posture of a patient. The posture-detecting device 74 is also in electrical communication with the processing unit 68. For example, the posture-detecting device 74 may provide a first reading or output when a patient is upright, and a second reading or output when a patient is at a different orientation. The posture-detecting device 74 may relay the data to the processing unit 68. When the processing unit 68 determines that a change from a first reading or output to the second reading or output occurs over a predetermined short, abrupt time (such as one or two seconds), the processing unit 68 may flag the abrupt change as a possible syncope.

While the transducer 66 is shown and described as being within the chamber 60 of the module 12, one or more transducers may alternatively be positioned on or within the pressure-detecting member 14. For example, the transducer(s) may be secured to the distal tip 24 of the sheath 26. The transducers may then be electrically connected to the processing unit 68 through insulated wiring that passes through and within the pressure-detecting member 14 and the module 12, or through a wireless connection. Locating the transducer(s) at the distal tip 24 may provide a strong, accurate, and reliable pressure reading.

The chamber 60 may also include a battery 75 that supplies power to the components within the chamber 60. The battery 75 may be rechargeable through the telemetry coil(s) 72. For example, the telemetry coil(s) 72 may receive RF power signals from a remote management system or external device (not shown in FIG. 3). The power signals may then be transmitted to the battery 75 in order to provide recharging power. Optionally, instead of the battery 75, the assembly 10 may be powered through electromagnetic RF signals received by the telemetry coil(s) 72 through an external RF telemetry device.

The transducer 66 may include a piezoelectric transducer, a strain gauge such as a piezo-resistive bridge bonded to the diaphragm 64, a pressure transducer that detects the deflection of the diaphragm 64 or tube, or the like. Various other devices, instead of transducers, may also be used to detect pressure pulses at the diaphragm 64. For example, a camera may be used to detect movement in the diaphragm 64 and relay the movement to the processing unit 68. Additionally, infrared or other light beams may be proximate the boundary of the diaphragm. When broken, the processing unit 68, which would be in electrical communication with the infrared detector, correlates the rate of light reception breaks as pressure pulses.

Additionally, the chamber 60 may include a blood analyzer 90 in electrical communication with the processing unit 68. The blood analyzer 90 is disposed within a fluid-tight channel 92 that passes from the blood inlet port 27 (shown in FIG. 1) to the blood outlet port 29 (shown in FIG. 1). Optionally, the blood analyzer is disposed within a fluid-tight channel that connects to a membrane in place of the blood inlet port 27. Blood samples may regularly pass through the channel 92 past the blood analyzer 90. The blood analyzer 90 detects the glucose level of the blood samples before the blood samples pass through the blood outlet port 29. If the blood glucose level is too low or too high, the blood analyzer 90 sends a signal to the processing unit 68, which may send an alert to an external device through the telemetry coil(s) 72.

Alternatively, the blood analyzer 90 may disposed within a fluid-tight channel 92 that passes from a membrane (that may replace the blood outlet 27) that allows interstitial body fluid having a glucose concentration representative of blood glucose to diffuse to an internal blood analyzer within the module 12. The interstitial body fluid diffuses through the membrane into the channel 92 and to the analyzer 90. The analyzer 90 detects the glucose level of the fluid. If the blood glucose level is too low or too high, the blood analyzer 90 sends a signal to the processing unit 68, which may send an alert to an external device through the telemetry coil(s) 72. As noted above, the membrane may be made of microporous poly propylene or 2-hydroxyethylene methacrylate.

Also, alternatively, the physiologic sensor assembly 10 may include less than the blood pressure, EKG, and glucose analyzer functionality, as described. For example, the physiologic sensor assembly 10 may include only the blood pressure functionality. Also, alternatively, the physiologic sensor assembly 10 may include only the blood pressure and EKG functionality.

Figure 4:
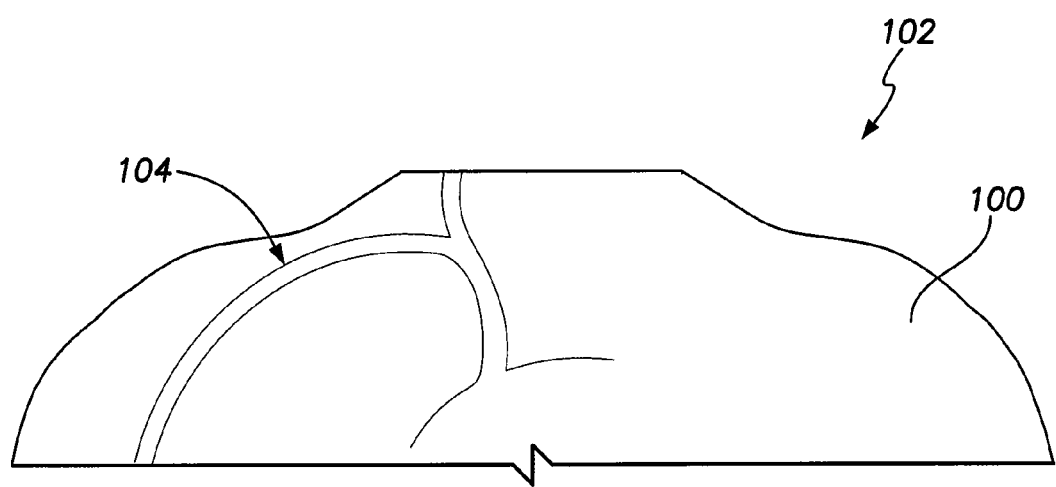
FIG. 4 illustrates a front view of a chest area of a patient with a simplified, internal view of a subclavian artery.

FIG. 4 illustrates a front view of a chest area 100 of a patient 102 with a simplified, internal view of a subclavian artery 104. Referring to FIGS. 1-4, the process of implanting the physiologic sensor assembly 10 will now be described. The physiologic sensor assembly 10 may be implanted into or proximate any artery or vein. However, the subclavian artery 104 is relatively close to the skin of the patient 102 and is easily accessible.

Figure 5:
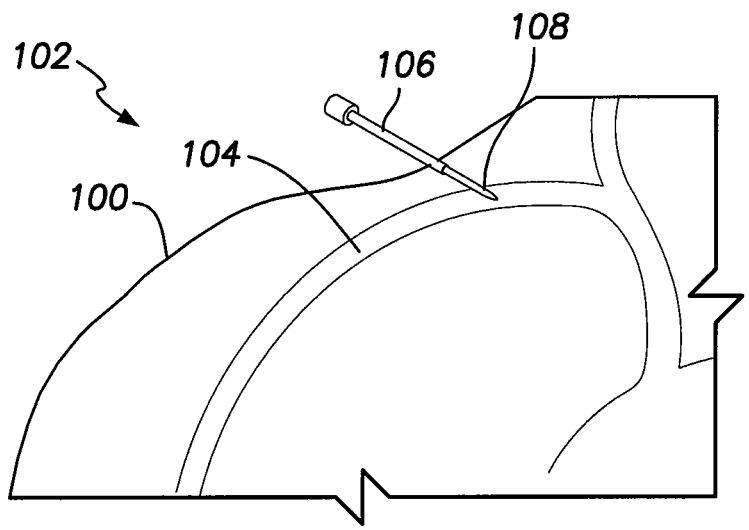
FIG. 5 illustrates a front view of a chest area of a patient and a hypodermic needle being inserted through the skin and into a subclavian artery, according to an embodiment.

FIG. 5 illustrates a front view of the chest area 100 of the patient 102 and a hypodermic needle 106 being inserted through the skin and into the subclavian artery 104, according to an embodiment. The hypodermic needle 106 is manipulated so that the distal end 108 of the needle 106 is introduced into the subclavian artery 104, where blood pressure will be measured.

Figure 6:
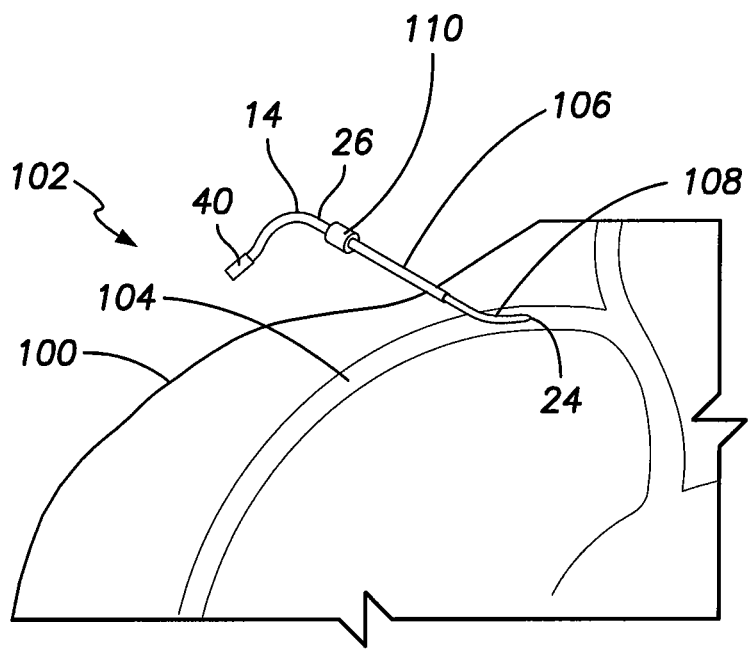
FIG. 6 illustrates a front view of a chest area of a patient with a pressure-detecting member being inserted into a proximal receiving end of a hypodermic needle, according to an embodiment.

FIG. 6 illustrates a front view of the chest area 100 of the patient 102 with the pressure-detecting member 14 being inserted into a proximal receiving end 110 of the hypodermic needle 106, according to an embodiment. Once the distal end 108 of the needle 106 is within the subclavian artery 104, the distal tip 24 (shown in FIG. 1) of the pressure-detecting member 14 is inserted into the proximal receiving end 110 of the needle 106. The diameter of the pressure-detecting member 14 is smaller than the internal diameter of the needle 106, and is therefore able to pass therethrough. The hypodermic needle 106 is then manipulated to introduce an end portion, such as approximately half, of the sheath 26 of the pressure-detecting member 14 into the subclavian artery 104. Once the portion of the sheath 26 is introduced into the subclavian artery 104, the hypodermic needle 106 is slid off the opposite end portion of the pressure-detecting member 14.

Figure 7:
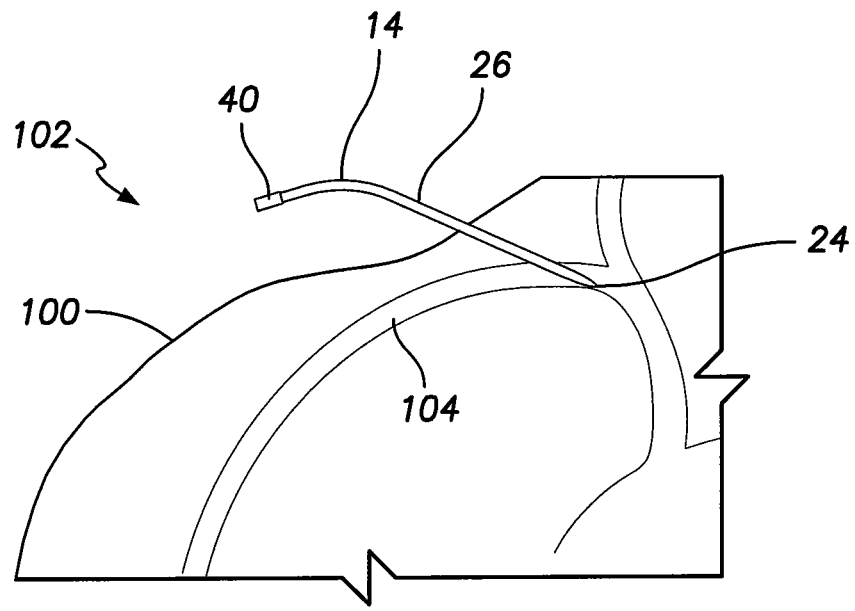
FIG. 7 illustrates a front view of a chest area of a patient with a portion of a pressure-detecting member within a subclavian artery, and a portion of the pressure-detecting member extending outside of the patient, according to an embodiment.

FIG. 7 illustrates a front view of the chest area 100 of the patient 102 with a portion of the pressure-detecting member 14 within the subclavian artery 104, and an end portion of the pressure-detecting member 14 extending outside of the patient 102, according to an embodiment. As shown, the connector 40 of the pressure-detecting member 14 is outside the patient 102. The opposite end portion of the pressure-detecting member 14, including the distal tip 24 of the sheath 26, may be within the subclavian artery 104.

Figure 8:
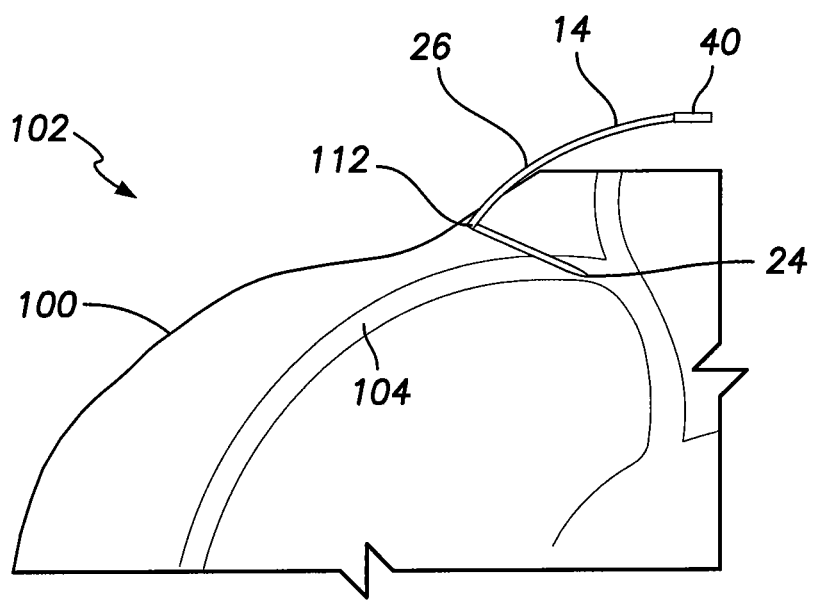
FIG. 8 illustrates a front view of a chest area of a patient with a portion of a pressure-detecting member within a subclavian artery, and a portion of the pressure-detecting member bent back and extending outside of the patient, according to an embodiment.

FIG. 8 illustrates a front view of the chest area 100 of the patient 102 with a portion of the pressure-detecting member 14 within the subclavian artery 104, and a portion of the pressure-detecting member 14 bent back and extending outside of the patient 102, according to an embodiment. A physician may grasp the connector 40 and bend it back toward the neck of the patient 102 in order to expose the skin of the patient proximate the injection site 112. In short, the physician may bend the exposed portion (outside of the patient) of the pressure-detecting member 14, in order to expose an incision site proximate the injection site 112. As shown, the pressure-detecting member 14 may have the distal tip 24 within the subclavian artery, while the sheath 26 is bent at the injection site 112, with the connector 40 being bent away from a linear relationship with the distal tip 24.

Figure 9:
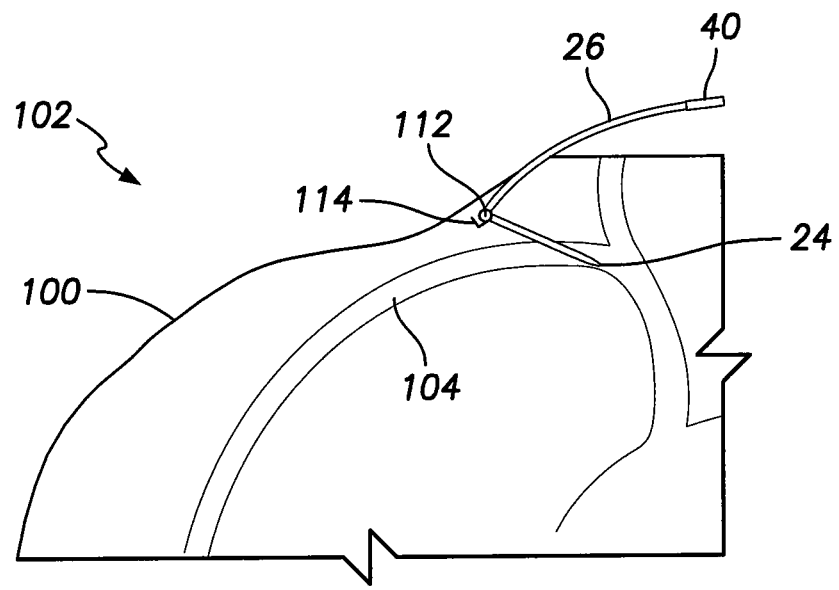
FIG. 9 illustrates a front view of a chest area of a patient with an incision made proximate an injection site, according to an embodiment.

FIG. 9 illustrates a front view of the chest area 100 of the patient 102 with an incision 114 made proximate the injection site 112, according to an embodiment. The physician makes the incision 114 proximate the injection site 112 after the distal tip 24 is implanted within the subclavian artery 104 and the connector 40 is bent back to expose the incision site.

Figure 10:
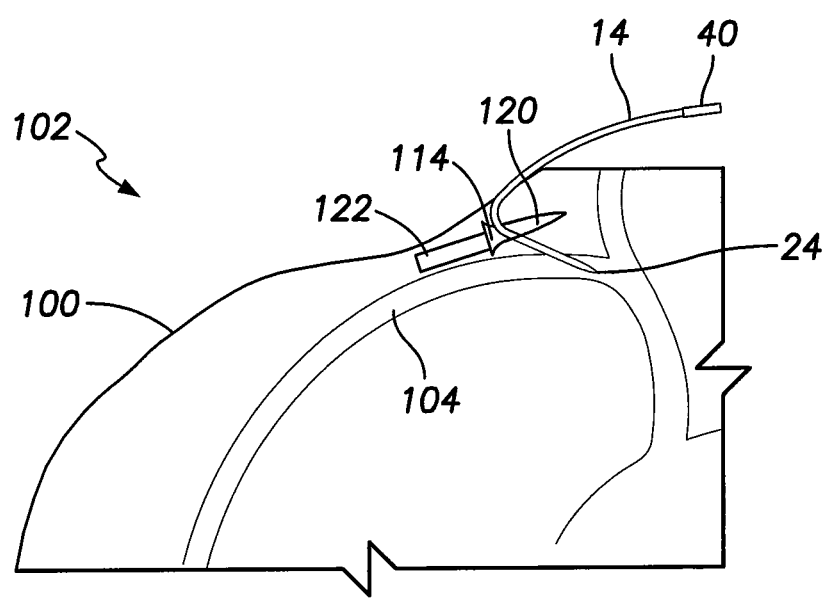
FIG. 10 illustrates a front view of a chest area of a patient with a retractor or dilator positioned through an incision, according to an embodiment.

FIG. 10 illustrates a front view of the chest area 100 of the patient 102 with a retractor or dilator 120 positioned through the incision 114, according to an embodiment. The physician manipulates the dilator 120 to form a subcutaneous pocket 122 within the chest area 100 of the patient. The pocket 122 may be formed in a direction opposite to that of the injection channel formed through injection site 112. The pocket 122 is formed to subcutaneously receive and retain the module 12 (shown in FIG. 1). After the pocket 122 is formed, the module 12 is connected to the connector 40 of the pressure-detecting member 14, as explained above.

Figure 11:
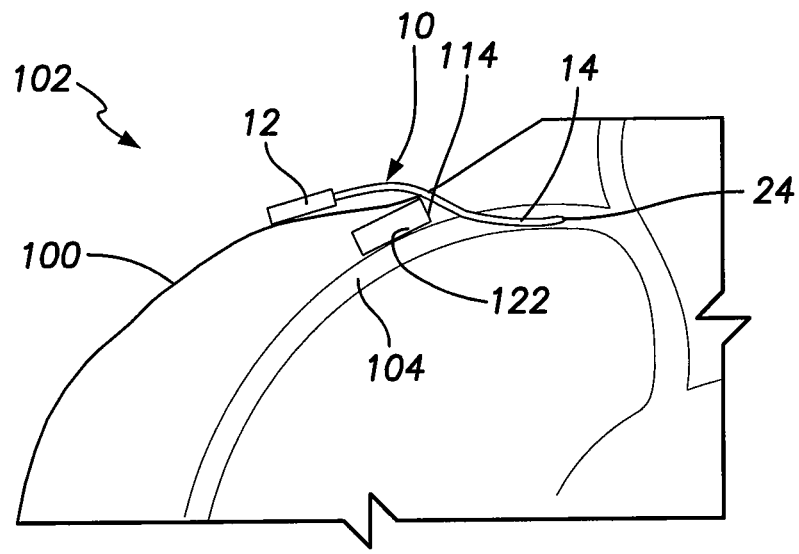
FIG. 11 illustrates a front view of a chest area of a patient with a module connected to a pressure-detecting member to form a physiologic sensor assembly, according to an embodiment.

FIG. 11 illustrates a front view of the chest area 100 of the patient 102 with the module 12 connected to the pressure-detecting member 14 to form the physiologic sensor assembly 10, according to an embodiment. Once the module 12 is connected to the pressure-detecting member 14, the module 12 may be inserted into the pocket 122.

Figure 12:
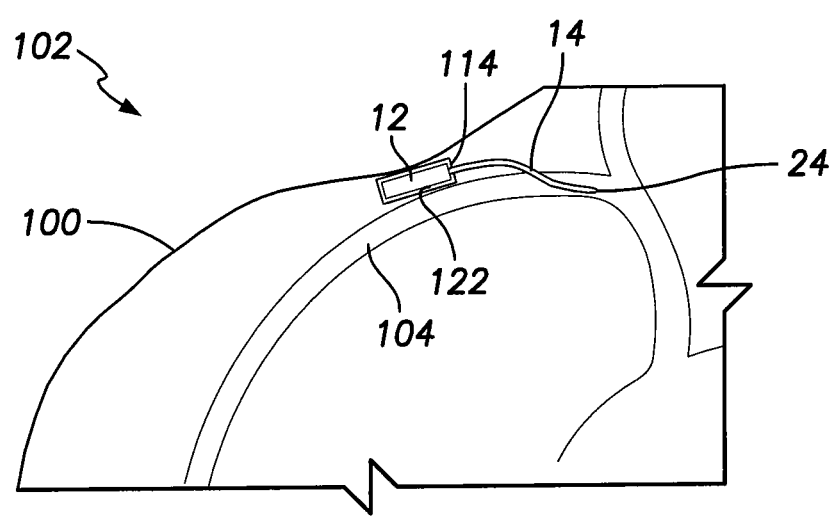
FIG. 12 illustrates a front view of a chest area of a patient with a module positioned within a pocket, according to an embodiment.

FIG. 12 illustrates a front view of the chest area 100 of the patient 102 with the module 12 positioned within the pocket 122, according to an embodiment. The module 12 is secured within the pocket 122. For example, the module 12 may be anchored within the pocket 122 through sutures, or the like. Optionally, the pocket 122 may be formed to conform to the shape of the module 12 so that no additional securing agents are needed. Once the module 12 is positioned within the pocket 12, the remainder of the pressure-detecting member 14 is moved into the subclavian artery 104 so that the entire assembly 10 is within the patient 102. The incision 114 is then sutured and closed, thereby containing the assembly 10 within the patient 102.

Thus, the two-piece design of the assembly 10 provides for an easy and efficient implantation process (as compared to previous processes for implanting a blood pressure monitor). Instead of implanting the assembly 10 deep into the patient 100, the assembly 10 may be implanted proximate the shoulder with the sheath 26 of the pressure-detecting member 14 being inserted into the subclavian artery 104, and the module 12 later being connected to the pressure-detecting member 14 and inserted into a pocket formed proximate the injection site 112. The two-piece assembly 10 allows for the pressure-detecting member 14 to be inserted into the hypodermic needle 106, and the needle 106 later being removed from the pressure-detecting member 14 so that the module 12 may be connected to the pressure-detecting member 14.

Alternatively, if the assembly 10 is formed as a single, integral unit, a physician would make an incision into the subclavian artery 104, and insert the distal tip 24 of the pressure-detecting member 14 therein. Then, the physician would make another incision and form the pocket 122 for the module 12 and move the module 12 into the pocket 122.

Figure 13:
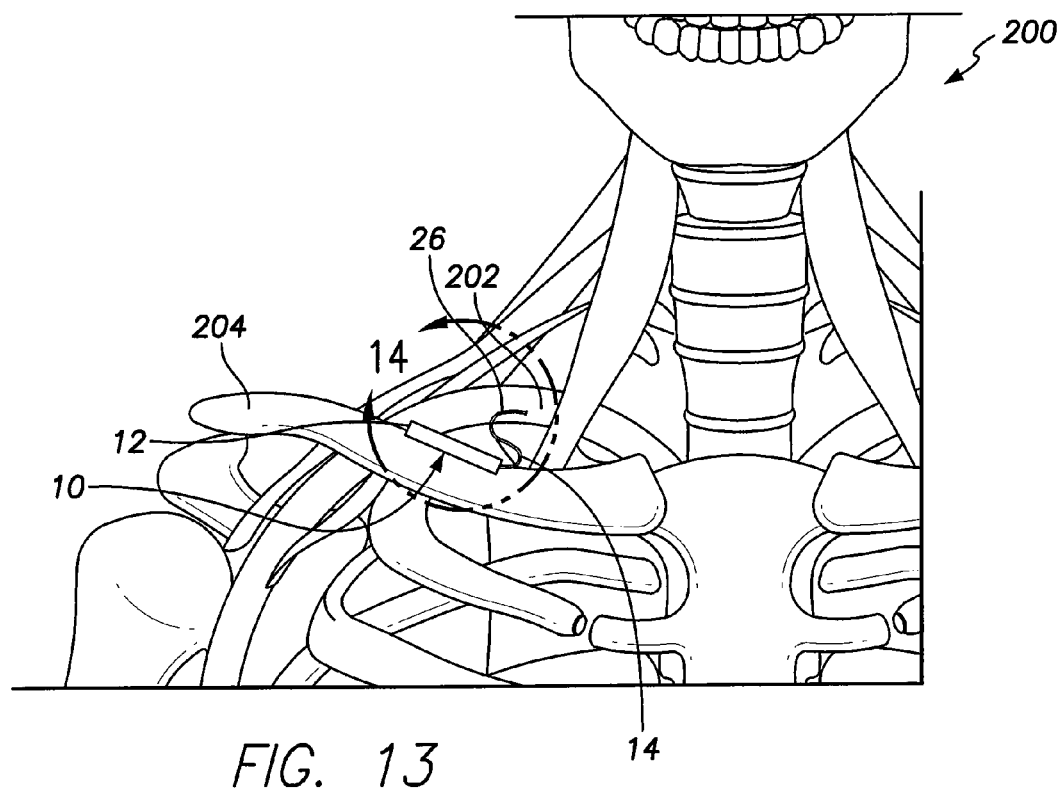
FIG. 13 illustrates a physiologic sensor assembly secured within a patient, according to an embodiment.
Figure 14:
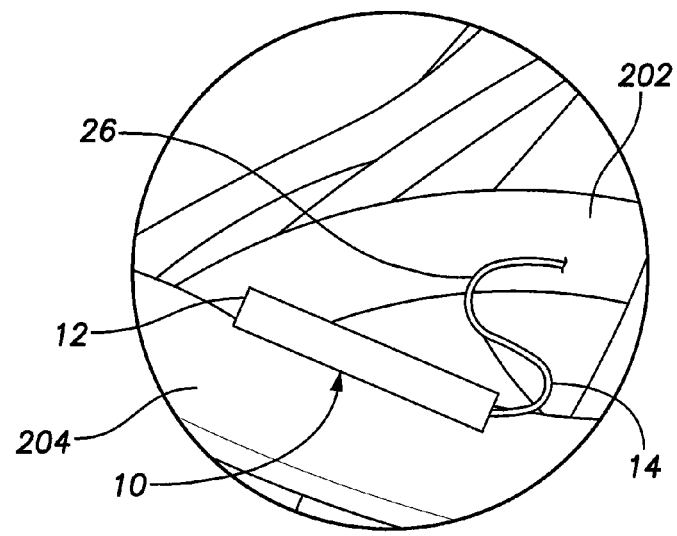
FIG. 14 illustrates a module of a physiologic sensor assembly secured to a clavicle, and a pressure-detecting member implanted into a subclavian artery, according to an embodiment.

FIG. 13 illustrates the physiologic sensor assembly 10 secured within a patient 200, according to an embodiment. FIG. 14 illustrates the module 12 of the physiologic sensor assembly 10 secured to a clavicle 204, and the pressure-detecting member 14 implanted into the subclavian artery 202. Referring to FIGS. 13 and 14, the distal tip 24 (not shown in FIG. 13) of the pressure-detecting member 14 is implanted into the subclavian artery 202. In this manner, the pressure-detecting member 14 may directly transmit blood pressure pulses to the processing unit 68 (not shown in FIG. 13) within the module 12.

The module 12 may be secured to the clavicle 204 of the patient. For example, the module 12 may be tied around the clavicle 204. Optionally, the module 12 may be secured to the clavicle 204 through fasteners, such as pins, screws, or the like.

Referring to FIGS. 1-3, 13, and 14, in operation, the physiologic sensor assembly 10 detects the blood pressure of the patient. Blood pressure pulses are transmitted from the pressure-detecting member 14 to the diaphragm 64. The transducer 66 transmits the pressure pulses to the processing unit 68, which may store the blood pressure data in the memory 70.

Additionally, the electrodes 25 may be used to perform an EKG. The EKG data may also be stored in the memory 70.

As noted above, the posture-detecting device 74 may be used to detect changes in patient posture. The processing unit 68 may be programmed to trigger a blood pressure and EKG correlation during a syncope event, such as when the posture-detecting device 74 relays a change in posture over a short period of time. During this time, the processing unit 68 may store blood pressure and EKG data from a predetermined period of time before the sudden, abrupt, detected change in posture, to a predetermined period of time after the detected change.

For example, the processing unit 68 may store a rolling 2 minute frame of blood pressure and EKG data at all times. The 2 minute frame may continually update that an instantaneous 2 minute frame is stored in a short term memory portion of the memory 70. When the posture-detecting device 74 detects a sudden, abrupt change in posture (for example, a dramatic change in posture over a short period of time, such as 1 or 2 seconds) through the posture-detecting device 74, the processing unit 68 stores the 2 minute time frame centered around the sudden, abrupt change in posture and correlates the EKG and/or blood glucose readings with the blood pressure readings over that time. The correlated data may then be sent to a remote management system through the telemetry coil(s) 72. In this manner, the data may be reviewed by a physician to determine a correlation between blood pressure, blood glucose, and EKG during a syncope event, for example.

As indicated, the telemetry coil(s) 72 are used to wirelessly transmit data to and from the physiologic sensor assembly 10. The physiologic sensor assembly 10, as described, is an implantable medical device (IMD). The blood pressure assembly 10 may be programmed and monitored by an external programmer or external home-based patient care system. For example, the blood pressure assembly may communicate with a base station within the patient's home or a programmer that is used by physicians to change settings within the physiologic sensor assembly 10 and/or retrieve data from the blood pressure assembly 10. The base station or external programmer device receives data from the IMD about the patient's blood pressure, EKG, and posture, as described above. For example, the physiologic sensor assembly 10, through the telemetry coil(s) 72, may transmit stored data or sensed physiological parameters to the base station. Based on the received data, the base station or external programmer device may adjust operating parameters for the physiologic sensor assembly 10.

Conventional external programmers and base stations employ near-field RF data communication techniques that facilitate communication between the physiologic sensor assembly 10 and a telemetry wand that is operatively connected to the base station. Typically, the wand of the base station or programmer is placed in close proximity to the physiologic sensor assembly 10 in order to establish a communication link. More recently, however, IMD telemetry assemblies have been proposed that employ far-field RF data communication techniques that do not require close proximity between the physiologic sensor assembly 10 and wand of the programmer or base station. Further, some systems do not include a separate and distinct telemetry wand, and the RF circuitry and antenna are embedded within the housing of the external programmer device or home base station.

Figure 15:
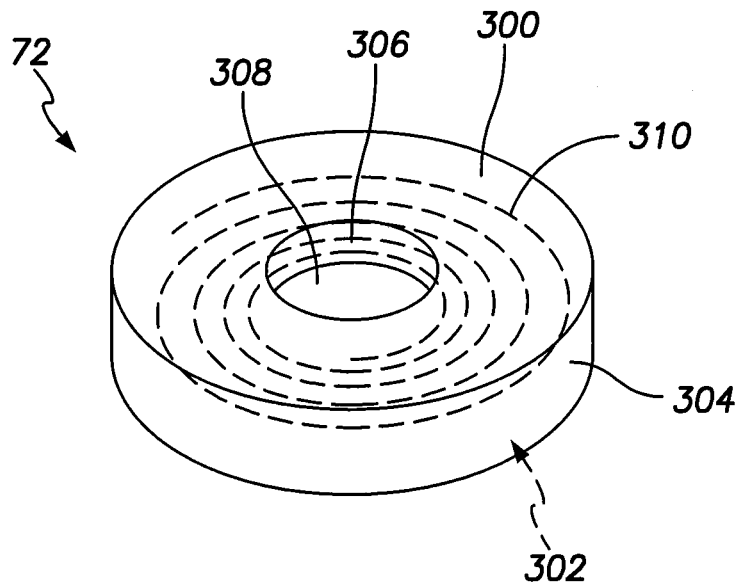
FIG. 15 illustrates an isometric view of a telemetry coil, according to an embodiment.

FIG. 15 illustrates an isometric view of the telemetry coil 72, according to an embodiment. As noted above, the internal operative chamber 60 (shown in FIG. 3) may house one or more telemetry coils 72. Each telemetry coil 72 includes opposed planar sides 300 and 302 that integrally connect to a peripheral edge 304 and an internal edge 306 that defines an opening 308. Optionally, the telemetry coil 72 may not include the opening 308, but instead, may be disc-shaped. Moreover, the telemetry coil 72 may be other shapes instead of circular. For example, the telemetry coil 72 may be shaped as a square, triangle, rectangle, trapezoid, or the like.

The telemetry coil 72 includes a coil group 310 encased therein. The coil group 310 may include windings arranged in a common plane parallel to the opposed planar sides 300 and 302 as well as the peripheral and internal edges 304 and 306. The coil group 310 may be formed of a single conductive wire.

Figure 16:
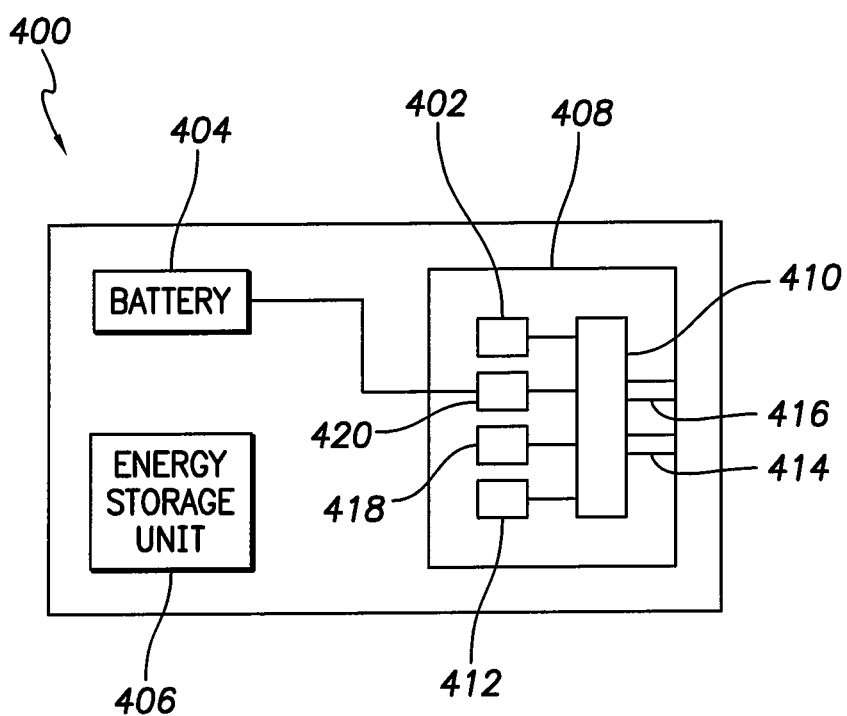
FIG. 16 illustrates a block diagram of a control block of a module, according to an embodiment.

FIG. 16 illustrates a block diagram of a control block 400 of the module 12, according to an embodiment. In the example of FIG. 16, the control block 400 includes a processor 402 (such as the processing unit 68 shown in FIG. 3) that is implemented to include all of the functionality of a physiologic sensor assembly. The control block 400 includes a rechargeable or non-rechargeable battery 404 (such as the battery 75 shown in FIG. 3) and an energy storage unit 406, such as a plurality of capacitors. The energy storage unit 406 may vary depending upon the functionality desired to be supplied by the control block 400.

Control logic may be provided on an integrated circuit (IC) 408 housed in the control block 400. The control logic includes various electronic components based on the desired functionality of the control block 400. By way of example, the control logic on the IC 408 includes the processor 402, a switching bridge 410, and analog-to-digital (A/D) converters 412. The switching bridge 410 includes multiple inputs 414 and 416 that are configured to be coupled to terminals connected to the electrodes 25 (shown in FIG. 1) and the telemetry coil(s) 72 (shown in FIG. 15). Optionally, the electrodes 25 and the telemetry coil(s) 72 may be directly connected through separate wires to the inputs 414 and 416 of the switch bridge 410. Optionally, more inputs 414, 416 may be used based on the number of electrodes and telemetry coils.

The IC 408 may also include a transceiver 418 that is configured to receive signals that are detected by the telemetry coil 72, as well as transmit signals to the telemetry coil 72 that are then wirelessly transmitted as RF energy. The transceiver 418 performs modulation upon outgoing data signals and performs demodulation upon incoming data signals. For example, the telemetry coil 72 may receive, in the RF energy, data signals such as commands, parameters, thresholds and the like. As one optional exemplary implementation for incoming data, the transceiver 418 may detect analog data signals sensed by the telemetry coil 72, convert the analog data signals into digital data packets and convey the data packets to the processor 402. As one optional exemplary implementation for outgoing data, the transceiver 418 receives data packets from the processor 402, converts the data packets to analog data signals and transmits the analog data signals over the telemetry coil 72. Optionally, for outgoing data transmissions, the transceiver 418 may packetize data segments in accordance with a predetermined wireless transmission protocol, such as by dividing an outgoing data stream into segments, and packetize each data segment with header and footer information. Similarly, incoming data transmissions may be formatted in accordance with a predetermined transmissions protocol. The transceiver 418 may temporally buffer incoming data transmissions, parse the stored inbound data stream for header and/or footer information, and extract the data content from the inbound data stream. The transceiver 418 may then convey data content to the processor 402 with or without reformatting and/or repackaging the data content.

With respect to the rechargeable battery 404, the telemetry coil 72 may receive, through RF energy, a power signal that is used to recharge the battery 404. The IC 408 includes a power conversion unit 420 that converts RF energy received on telemetry coil 72 into a power supply signal that can recharge the battery 404 (for example, to a desired voltage range and/or current level). As explained below, the RF energy generates a magnetic field, which, in turn, induces a current within the telemetry coil 72 that is used to recharge the battery 404.

When the physiologic sensor assembly 10 is located deep within patient anatomy, as compared with subcutaneous implants, the signals transmitted to/from the telemetry coil 72 (shown in FIG. 15) may be weaker. Optionally, more or fewer coil windings may be included within telemetry coil 72 depending upon whether the assembly 10 is intended to be implanted shallower or deeper. Embodiments described herein may utilize multiple telemetry coils 72 having waved multi-loop coil groups. Each coil group represents an inductor. By joining the coil groups electrically in series, a series of inductors are formed to achieve coupling and signal linkage through telemetry with desired implanted or external components.

Figure 17:
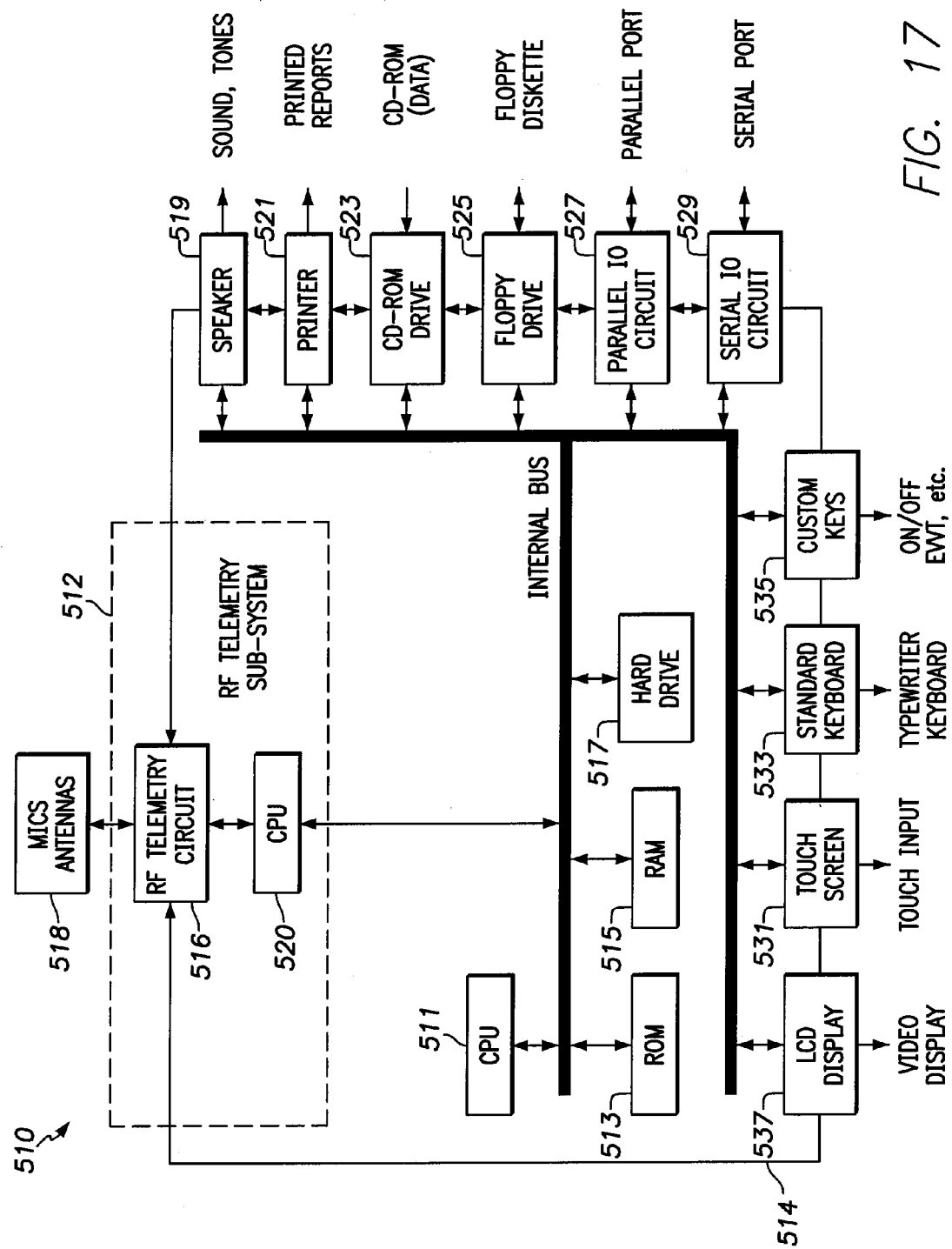
FIG. 17 illustrates a functional block diagram of an external device, formed according to an embodiment.

FIG. 17 illustrates a functional block diagram of an external device 510, formed according to an embodiment. The external device 510 may represent a handheld portable tablet-type programmer device used by physicians and others to communicate with, collect data from, program and re-program, the physiologic sensor assembly 10 (shown in FIG. 1, for example). Optionally, the device 510 may be a patient care system, such as the Merlin® home patient care system offered by St. Jude Medical. The device 510 includes an RF telemetry subsystem 512 that communicates with the physiologic sensor assembly 10, such as through the telemetry coil(s) 72 (shown in FIG. 3, for example), and/or network 514. The telemetry subsystem 512 includes an RF telemetry circuit 516 operatively connected to MICS antennas 518. The circuit 516 is also operatively connected to a controller or processing unit 520.

The external device 510 may be a workstation, a portable computer, an IMD programmer, a PDA, a cell phone, and the like. The external device 510 includes an internal bus that connects/interfaces with a Central Processing Unit (CPU) 511, ROM 513, RAM 515, a hard drive 517, speaker 519, a printer 521, a CD-ROM drive 523, a floppy drive 525, a parallel I/O circuit 527, a serial I/O circuit 529, a display 530, a touch screen 531, a standard keyboard connection 533, custom keys 535, and the telemetry subsystem 512. The internal bus is an address/data bus that transfers information between the various components described herein. The hard drive 517 may store operational programs as well as data, such as waveform templates and detection thresholds.

The CPU 511 typically includes a microprocessor, a micro-controller, or equivalent control circuitry, designed specifically to control interfacing with the external device 510 and with the physiologic sensor assembly 10. The CPU 511 may include RAM or ROM memory, logic and timing circuitry, state machine circuitry, and I/O circuitry to interface with the physiologic sensor assembly 10. The touch screen 524 may display graphic information relating to the physiologic sensor assembly 10. The touch screen 531 accepts a user's touch input when selections are made. The keyboard 533 (e.g., a typewriter keyboard) allows the user to enter data to the displayed fields, as well as interface with the telemetry subsystem 512. Furthermore, custom keys 535 turn on/off (e.g., EVVI) the external device 510. The printer 521 prints copies of reports for a physician to review or to be placed in a patient file, and the speaker 519 provides an audible warning (e.g., sounds and tones) to the user. The parallel I/O circuit 527 interfaces with a parallel port The serial I/O circuit 529 interfaces with a serial port. The floppy drive 525 accepts diskettes. Optionally, the floppy drive 525 may be a USB port or other interface capable of communicating with a USB device such as a memory stick. The CD-ROM drive 523 accepts CD ROMs.

As noted above, the telemetry subsystem 512 includes the central processing unit (CPU) 520 in electrical communication with the RF telemetry circuit 516. The telemetry circuit 516 is configured to communicate with the telemetry coil(s) 72 (shown in FIGS. 3 and 15) of the physiologic sensor assembly 10. Additionally, the telemetry circuit 516 may transmit power signals to the telemetry coil(s) 72, which may be used to charge the physiologic sensor assembly 10.

The telemetry circuit 516 may be connected to a telemetry wand. The external device 510 may wirelessly communicate with the physiologic sensor assembly 10 and utilize protocols, such as Bluetooth, GSM, infrared wireless LANs, HIPERLAN, 3G, satellite, as well as circuit and packet data protocols, and the like.

Figure 18:
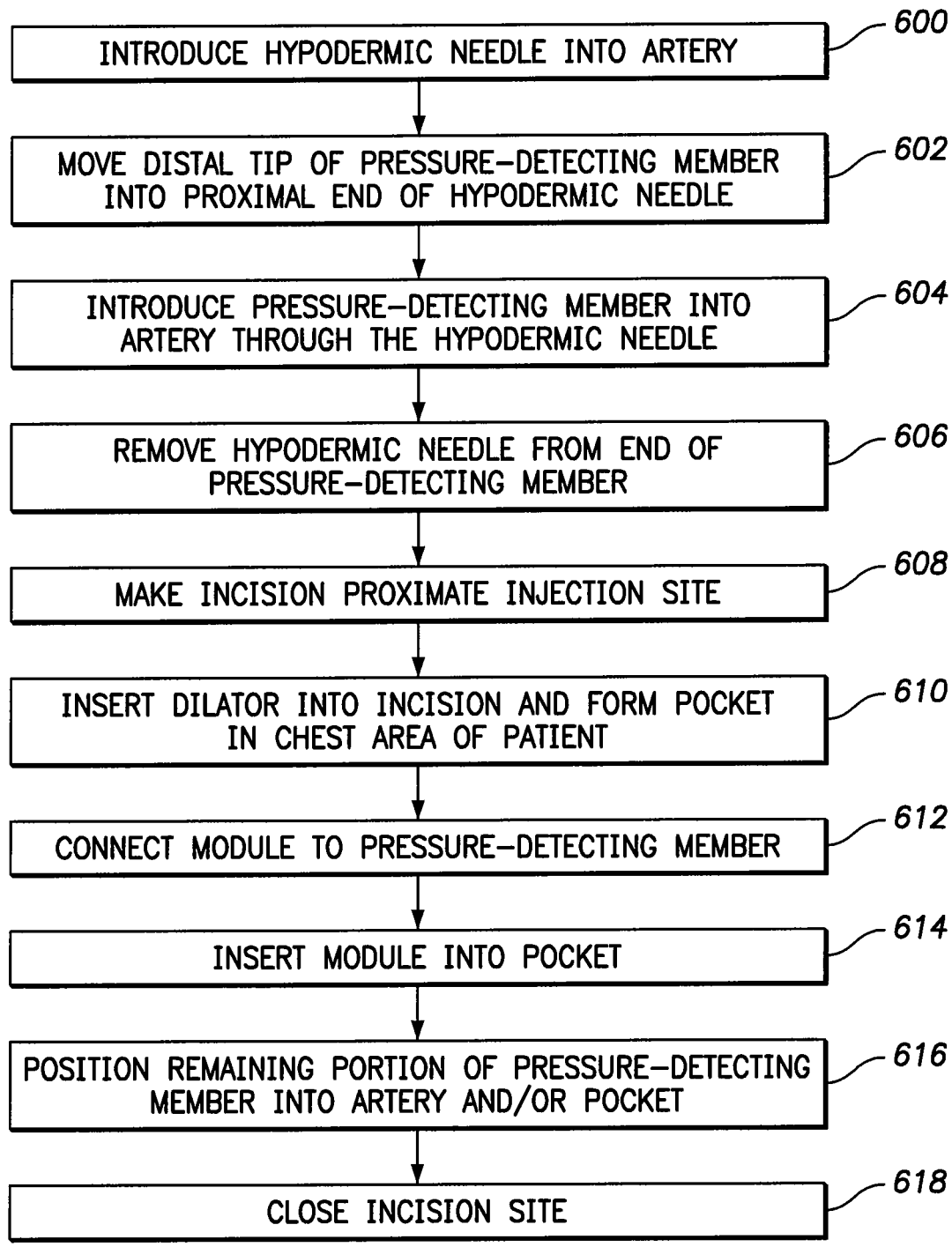
FIG. 18 illustrates a flow chart of a process of implanting a physiologic sensor assembly into a patient, according to an embodiment.

FIG. 18 illustrates a flow chart of a process of implanting a physiologic sensor assembly into a patient, according to an embodiment. Before the process begins, the pressure-detecting member of the physiologic sensor assembly may be disconnected from the module.

At 600, a hypodermic needle is introduced into an artery of a patient. For example, the hypodermic needle may be introduced into the subclavian artery. Optionally, instead of hypodermic needle, a physician may simply make an incision into the skin of the patient and gain access to the artery.

Then, at 602, a first end portion including a distal tip of the pressure-detecting member is moved into a proximal end of the hypodermic needle. The distal tip is moved toward a distal end of the hypodermic needle so that the distal tip may be introduced into the artery. Optionally, a physician may simply insert the distal tip of the pressure-detecting member directly into the artery.

At 604, the hypodermic needle is then manipulated to introduce the first end portion, including the distal tip, of the pressure-detecting member into the artery. The distal tip of the pressure-detecting member is inserted into the artery, while a second end portion (including the connector) that is opposite the first end portion of the pressure-detecting member extends outside of the patient.

Then, at 606, the hypodermic needle is removed from the exposed end of the pressure-detecting member. For example, the hypodermic needle may be slid off the second end portion of the pressure-detecting member that is outside of the patient.

At 608, a physician makes an incision proximate the injection site from which the hypodermic needle was removed. The incision site may be made in a direction that is opposite to the direction in which the hypodermic needle was introduced into the patient. Optionally, if the physician made an incision to insert the distal tip of the pressure-detecting member into the artery, the physician may simply use that incision to form a pocket in an opposite direction from the portion of the pressure-detecting member that is inserted in the artery.

At 610, a dilator or retractor is inserted into the incision and used to form a pocket within the patient's anatomy. The pocket is formed and sized to receive and retain the module.

At 612, the module is connected to the pressure-detecting member. Next, at 614, the module is inserted into the pocket formed by the dilator or retractor. At 616, any remaining portion of the pressure-detecting member outside of patient is then positioned into the artery and/or the pocket.

Finally, at 618, with the module inside the pocket and the pressure-detecting member in the artery, the incision is closed, such as through sutures.

Figure 19:
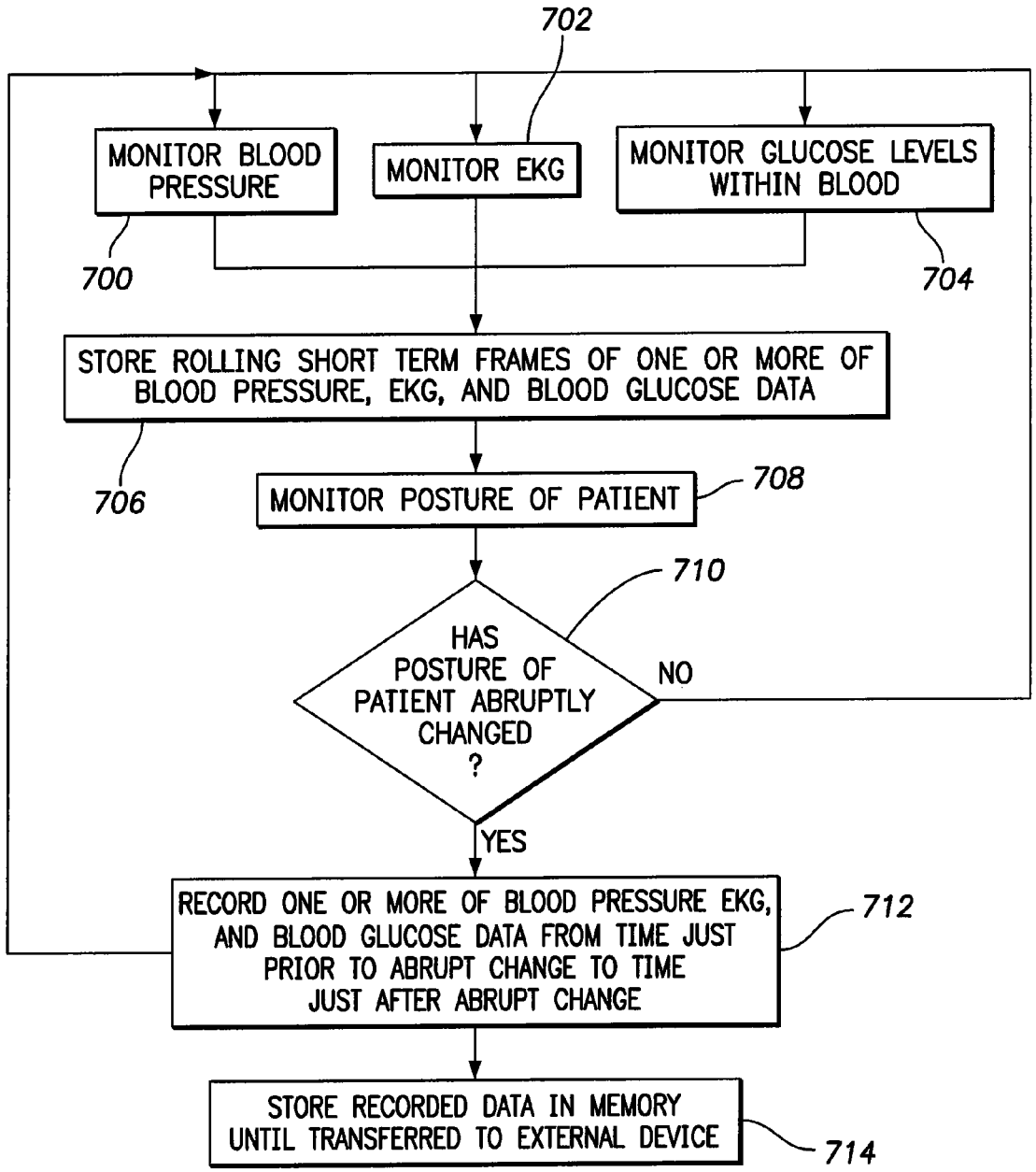
FIG. 19 illustrates a flow chart of a monitoring process of an implanted physiologic sensor assembly, according to an embodiment.

FIG. 19 illustrates a flow chart of a monitoring process of an implanted physiologic sensor assembly, according to an embodiment. The process begins at 700, 702, and 703, in which the physiologic sensor assembly monitors blood pressure (700), EKG (702), and glucose levels within the blood (704), as discussed above.

At 706, the processing unit of the assembly stores a rolling short term frame of blood pressure, EKG, and blood glucose levels a short term memory section of the memory. For example, the rolling short term frame may be a 2 minute frame of data. If the frame starts at 0 seconds, the frame is recorded until the 2 minute mark. At 2:01, the data collected at 0 seconds is erased by the data collected at 2:01, and the process continues in such a manner.

Simultaneous to 700, 702, and 704, the posture of the patient is monitored at 708. The posture-detecting device is used to detect a pre-calibrated upright position and variances therefrom. The processing unit of the blood pressure senor assembly may be programmed to determine sudden and abrupt changes from the pre-calibrated upright position. For example, a change from the pre-calibrated upright position to a position that is perpendicular to the upright position over a very short period of time, such as 1-2 seconds (as detected, for example, by an accelerometer), may be determined to be an abrupt change in posture.

Then, at 710, the physiologic sensor assembly determines if the posture of the patient has abruptly changed. If the patient posture has not abruptly changed, the process returns to 700, 702, and 704.

If, however, the processing unit does detect an abrupt change in posture, the process proceeds to 712, in which the processing unit records and stores the blood pressure data, EKG, and blood glucose data from a time frame that is centered about the instant of abrupt change. For example, the time frame may be from 1 minute before the abrupt change to 1 minute after the abrupt change. The recorded data is stored in long term memory, for example. At 714, the recorded data is stored in the memory until transferred to an external device, such as through telemetry as discussed above. Once the recorded data is transferred to the external device, the recorded data may be deleted from memory, and the process returns to 700, 702, and 704. Notably, even when the data is recorded, the process continues to 700, 702, and 704. Indeed, the process may continuously and constantly perform 700, 702, and 704.

A physician or caretaker may then review the patient's blood pressure, EKG, and blood glucose levels from a time just prior to the abrupt change, which may be a syncope event, to a time just after the abrupt change. In this manner, the physician or caretaker may be able to correlate changes in blood pressure, EKG, and blood glucose with the abrupt change, such as a syncope event.

Alternatively, the process may monitor less than all of blood pressure, EKG, and blood glucose levels. For example, the process may monitor only blood pressure and EKG, or EKG and blood glucose.

Additionally, the physiologic sensor assembly 10 shown in FIG. 1, for example, may be communicatively linked with other implantable devices within the patient, such as a cardiac pacemaker, defibrillator, and the like, to monitor operation thereof, and correlate blood pressure, EKG, and/or blood glucose levels with operation of the other implantable devices.

Figure 20:
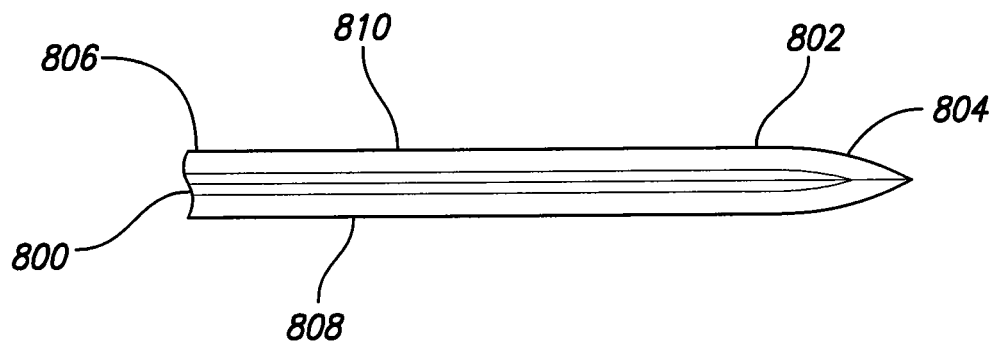
FIG. 20 illustrates a pressure-detecting member within a breakaway needle, according to an embodiment.

FIG. 20 illustrates a pressure-detecting member 800 within a breakaway needle 802, according to an embodiment. The pressure-detecting member 800 may be similar to the pressure-detecting member 14 described above.

The breakaway needle 802 includes a distal, insertion tip 804 and a proximal end 806. The breakaway needle 802 includes first and second longitudinal halves 808 and 810 that form an internal passage when connected together. The pressure-detecting member 800 is contained within the longitudinal halves 808 and 810. The breakaway needle 802 is configured to split open along seams that connect the halves 808 and 810.

Figure 21:
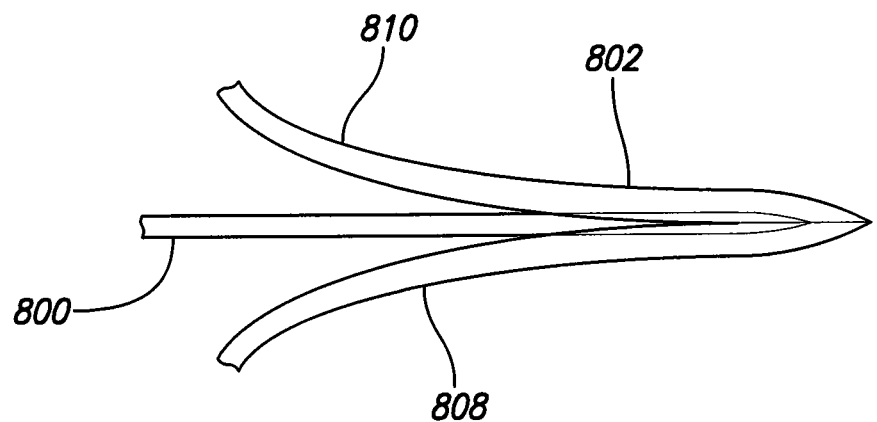
FIG. 21 illustrates a breakaway needle being separated, leaving a pressure-detecting member in place, according to an embodiment.

FIG. 21 illustrates the breakaway needle 802 being separated, leaving the pressure-detecting member 800 in place, according to an embodiment. Referring to FIGS. 20 and 21, a module (not shown in FIGS. 20 and 21), such as the module 12 of the physiologic sensor assembly 10, may be permanently affixed to the pressure-detecting member 800. Implantation may be facilitated using the breakaway needle 802, which may be similar to the breakaway needle described in U.S. Pat. No. 4,702,735, entitled "Assembly of Breakway Needle and Catheter," which is hereby incorporated by reference in its entirety. The breakaway needle 802 is configured to split along the entire length between the halves 808 and 810. A physician manipulates the breakaway needle 802 so that the insertion tip 804 pierces a patient's vasculature, such as an artery. Then, the pressure detecting member 800 is inserted into the vasculature through the breakaway needle 802. The halves 808 and 810 of the breakaway needle 802 are peeled away, leaving the pressure detecting member 800 in place. Next a small pocket is made as described in FIG. 10, and the physiologic sensor assembly 10 is implanted as shown in FIG. 11.

Alternatively, the halves 808 and 810 may include a connecting member that secures the halves 808 and 810 together. For example, the halves 808 and 810 may be connected through snapable, latchable, press-fit, or the like connections along a longitudinal seam. The halves 808 and 810 may even be connected through zippers. In order to separate the halves, the connecting members may be disengaged, and the halves 808 may simply be separated and removed without being peeled back from one another.

The breakaway needle 802 may include a U-chapped channel and a flat leaf that runs the length of the channel. The flat leaf may have overlapping tab-snaps at the insertion tip 804. The flat leaf may roll up as the needle channel is pulled out, and then separates when the needle is just outside the body.

Alternatively, a needle with a close-fitting split-able polymer sheath may also be used to place the pressure detecting member 800 into the vasculature. In this embodiment, the needle with the close-fitting outer sheath may be used to penetrate the vasculature. Once in the vasculature, the needle is removed from the split-able sheath. The split-able sheath remains in the vasculature. The pressure detecting member 800 is then inserted through the split-able sheath into the vasculature. Next the split-able sheath is pulled back and removed by pealing the split-able sheath apart.

Figure 22:
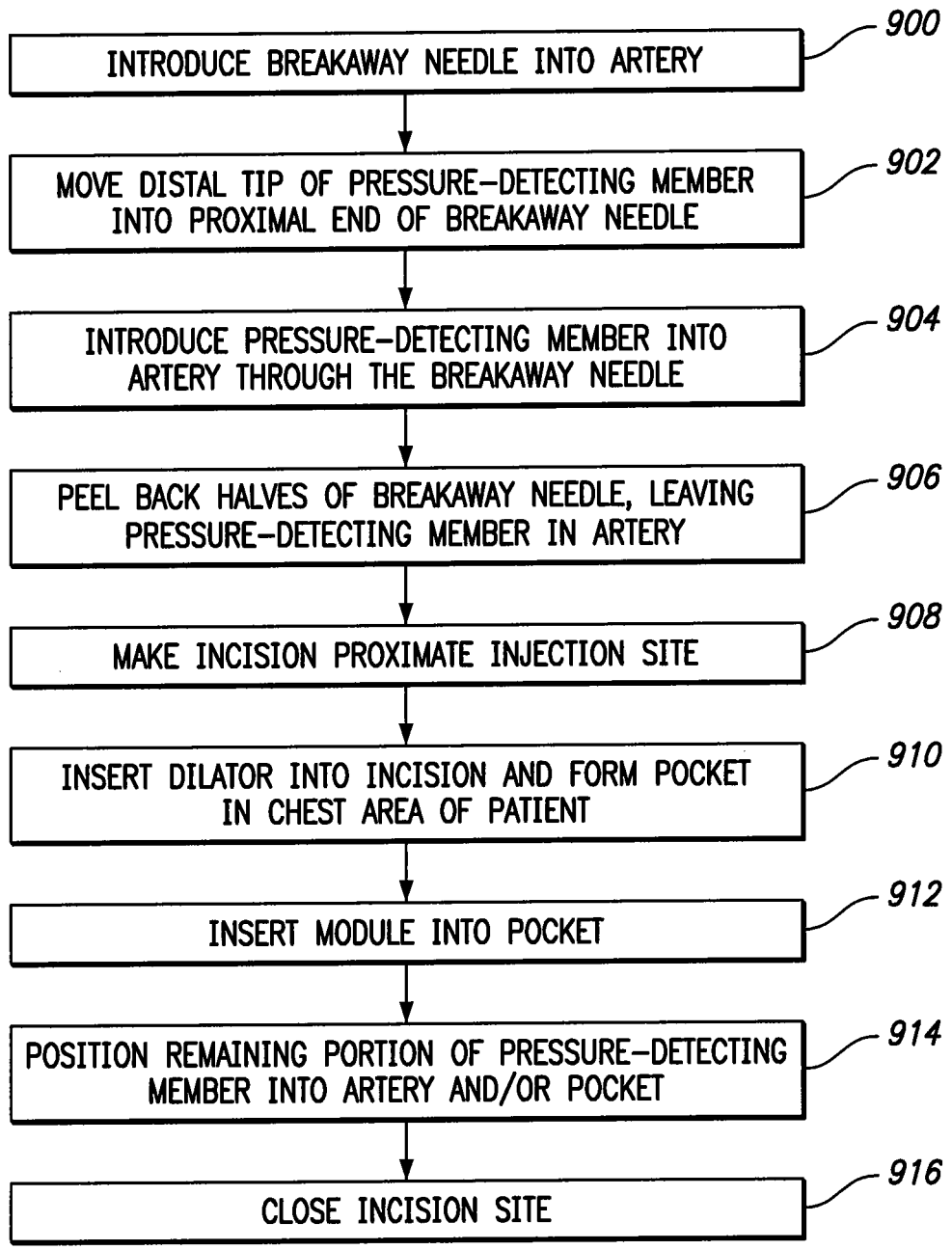
FIG. 22 illustrates a flow chart of a process of implanting a physiologic sensor assembly into a patient, according to an embodiment.

FIG. 22 illustrates a flow chart of a process of implanting a physiologic sensor assembly into a patient, according to an embodiment. At 900, a breakaway needle is inserted into an artery of a patient. At 902, a distal tip of a pressure-detecting member may be moved into a proximal receiving end of the breakaway needle. 902 may be performed prior to or after 900. The pressure-detecting member may be permanently secured to a module of a physiologic sensor. Optionally, the pressure-detecting member and the module may be separate and distinct, dis-connectable components, as described above with respect to FIG. 2a, for example.

At 904, the pressure-detecting member is introduced into the artery through the breakaway needle. Once the pressure-detecting member is at a desired position, longitudinal halves of the breakaway needle are peeled back and removed from the artery at 906, leaving the pressure-detecting member in the artery.

Next, at 908, a physician makes an incision proximate the injection site. Optionally, 908 may be performed prior to the breakaway needle is inserted into the artery.

At 910, a dilator may be inserted into the incision to form a pocket in the chest area of the patient. Then, at 912, the module, which may be permanently attached to the pressure-detecting member, is inserted into the pocket. At 914, the remaining portion of the pressure-detecting member is positioned into the artery and/or the pocket. Finally, at 916, the incision site is closed, such as through sutures.

Thus, embodiments provide systems and methods of implanting a physiologic sensor assembly into a patient. The process of implanting is quicker and easier than known processes of implanting an internal blood pressure monitor. Embodiments provide therapeutic and diagnostic information to the patient and caregiver.

Embodiments also provide systems and methods for monitoring various physiological characteristics of a patient with a single physiologic sensor assembly that is implanted within the patient.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

The invention claimed is:

1. An implantable physiologic sensor assembly configured to be implanted within a patient, the assembly comprising:
a module that houses an internal operative chamber having a processing unit configured to sense at least one physiological attribute of the patient, wherein the module is configured to be subcutaneously positioned within the patient; and
a pressure-detecting member having a first end portion configured to be inserted into vasculature of the patient, and a second end portion having a connector configured to be coupled to a connector port of the module, the connector port having a membrane configured to retain a pressure-transmitting fluid within the connector port prior to the connector port receiving and retaining the connector.

2. The assembly of claim 1, wherein the internal operative chamber comprises a flexible diaphragm that abuts the second end portion of the pressure-detecting member when the second end portion is connected to the module.

3. The assembly of claim 2, wherein the internal operative chamber further comprises a transducer operatively connected to the diaphragm, wherein the transducer is configured to detect pressure pulses from pumping blood within the vasculature of the patient that are transmitted into the pressure-detecting member.

4. The assembly of claim 1, wherein the connector comprises a connector connected to a sheath.

5. The assembly of claim 4, wherein the sheath comprises a cannula.

6. The assembly of claim 4, wherein the connector port is configured to receive and securely retain the connector of the pressure-detecting member.

7. The assembly of claim 6, wherein one of the connector port or the connector comprises a detent, and wherein the other of the connector port or the connector comprises a reciprocal groove configured to securely retain the detent so that the module is secured to the pressure-detecting member.

8. The assembly of claim 6, wherein the connector port further comprises:
a needle tip.

9. The assembly of claim 1, further comprising at least one electrode extending from the module, wherein the at least one electrode is configured for use in connection with an electrocardiogram.

10. The assembly of claim 1, wherein the internal operative chamber houses a blood analyzer configured to monitor the glucose level of a blood sample.

11. The assembly of claim 10, wherein the module comprises a blood inlet port and a blood outlet port connected by a channel, wherein the blood analyzer is disposed within the channel.

12. The assembly of claim 1, wherein the processing unit is configured to detect pressure pulses transmitted from the pressure-detecting member.

13. The assembly of claim 1, wherein the internal operative chamber comprises a memory configured to store one or more of blood pressure data, electrocardiogram data, or blood glucose data.

14. The assembly of claim 1, wherein the internal operative chamber comprises at least one telemetry coil configured to communicate with an external device.

15. The assembly of claim 14, wherein the at least one telemetry coil is configured to receive electromagnetic RF power signals to provide power to the assembly.

16. The assembly of claim 1, wherein the internal operative chamber comprises a posture-detecting device configured to detect a posture of the patient.

* * * * *